US011504408B2

(12) United States Patent
Longo et al.

(10) Patent No.: US 11,504,408 B2
(45) Date of Patent: Nov. 22, 2022

(54) FASTING-MIMICKING DIET (FMD) BUT NOT WATER-ONLY FASTING PROMOTES REVERSAL OF INFLAMMATION AND IBD PATHOLOGY

(71) Applicant: UNIVERSITY OF SOUTHERN CALIFORNIA, Los Angeles, CA (US)

(72) Inventors: Valter D. Longo, Playa Del Rey, CA (US); Min Wei, West Covina, CA (US); Priya Rangan, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/976,952

(22) PCT Filed: Mar. 15, 2019

(86) PCT No.: PCT/US2019/022488
§ 371 (c)(1),
(2) Date: Aug. 31, 2020

(87) PCT Pub. No.: WO2019/178486
PCT Pub. Date: Sep. 19, 2019

(65) Prior Publication Data
US 2020/0390833 A1  Dec. 17, 2020

Related U.S. Application Data

(60) Provisional application No. 62/735,147, filed on Sep. 23, 2018, provisional application No. 62/734,475, filed on Sep. 21, 2018, provisional application No. 62/643,296, filed on Mar. 15, 2018.

(51) Int. Cl.
| | |
|---|---|
| *A61K 35/747* | (2015.01) |
| *A23L 33/135* | (2016.01) |
| *A23L 3/44* | (2006.01) |
| *A61K 9/16* | (2006.01) |
| *A61K 9/48* | (2006.01) |
| *A61K 35/745* | (2015.01) |
| *A61K 45/06* | (2006.01) |
| *A61K 35/00* | (2006.01) |

(52) U.S. Cl.
CPC .............. *A61K 35/747* (2013.01); *A23L 3/44* (2013.01); *A23L 33/135* (2016.08); *A61K 9/16* (2013.01); *A61K 9/48* (2013.01); *A61K 35/745* (2013.01); *A61K 45/06* (2013.01); *A61K 2035/115* (2013.01)

(58) Field of Classification Search
None
See application file for complete search history.

(56) References Cited

U.S. PATENT DOCUMENTS

| | | |
|---|---|---|
| 8,211,700 B2 | 7/2012 | Longo |
| 8,728,815 B2 | 5/2014 | Longo |
| 8,865,646 B2 | 10/2014 | Longo |
| 9,237,761 B2 | 1/2016 | Longo et al. |
| 9,386,790 B2 | 7/2016 | Longo et al. |
| 10,015,980 B2 | 7/2018 | Longo et al. |
| 10,172,839 B2 | 1/2019 | Longo et al. |
| 10,246,446 B2 | 4/2019 | Longo et al. |
| 10,433,576 B2 | 10/2019 | Longo et al. |
| 10,660,932 B2 | 5/2020 | Longo et al. |
| 2003/0044946 A1 | 3/2003 | Longo |
| 2007/0134391 A1* | 6/2007 | Prakash ................. A23L 27/36 426/548 |
| 2011/0118528 A1 | 5/2011 | Longo et al. |
| 2013/0045215 A1 | 2/2013 | Longo et al. |
| 2013/0316948 A1 | 11/2013 | Longo |
| 2014/0328863 A1 | 11/2014 | Longo |
| 2015/0133370 A1 | 5/2015 | Longo |
| 2016/0220620 A1 | 8/2016 | Mazo et al. |
| 2016/0271188 A1* | 9/2016 | Berry .................... A61K 9/19 |
| 2016/0303056 A1 | 10/2016 | Longo et al. |
| 2016/0324193 A1 | 11/2016 | Longo et al. |
| 2016/0331016 A1 | 11/2016 | Longo et al. |
| 2017/0027217 A1 | 2/2017 | Longo et al. |
| 2017/0035093 A1 | 2/2017 | Longo et al. |
| 2017/0035094 A1 | 2/2017 | Longo et al. |
| 2017/0232053 A1 | 8/2017 | Longo et al. |
| 2017/0296600 A1 | 10/2017 | Rangavajla et al. |

(Continued)

FOREIGN PATENT DOCUMENTS

| | | |
|---|---|---|
| KR | 20160066724 A | 6/2016 |
| KR | 20170058710 A | 5/2017 |

(Continued)

OTHER PUBLICATIONS

Brandhorst, S. et al., "Short-term calorie and protein restriction provide partial protection from chemotoxicity but do not delay glioma progression," Experimental Gerontology 48 (2013), pp. 1120-1128.
Brandhorst, S. et al., "A Periodic Diet that Mimics Fasting Promotes Multi-System Regeneration, Enhanced Cognitive Performance, and Healthspan," Cell Metabolism 22, Jul. 7, 2015, pp. 86-99.
Cheng, C.-W. et al., "Prolonged Fasting Reduces IGF-1/PKA to Promote Hematopoietic-Stem-Cell-Based Regeneration and Reverse Immunosuppression," Cell Stem Cell 14, Jun. 5, 2014, pp. 810-823.
Cheng, C.-W. et al., "Fasting-Mimicking Diet Promotes Ngn3-Driven Beta-Cell Regeneration to Reverse Diabetes," Cell 168 (2017), pp. 775-788.

(Continued)

*Primary Examiner* — Brian Gangle
(74) *Attorney, Agent, or Firm* — Brooks Kushman P.C.

(57) ABSTRACT

A method for treating autoimmune and/or inflammatory disease includes a step of identifying a subject exhibiting symptoms of autoimmune and/or inflammatory disease administering a fasting mimicking diet. A probiotic composition for gastrointestinal autoimmune and/or inflammatory disease *Bacteroides acidifaciens, Bifidobacterium choerinum*, and combinations thereof is also provided.

15 Claims, 16 Drawing Sheets

(56) References Cited

U.S. PATENT DOCUMENTS

| | | | |
|---|---|---|---|
| 2017/0325493 | A1 | 11/2017 | Longo et al. |
| 2017/0333492 | A1 | 11/2017 | Kweon et al. |
| 2018/0228198 | A1 | 8/2018 | Longo et al. |
| 2019/0029301 | A1 | 1/2019 | Longo et al. |
| 2019/0276445 | A1 | 9/2019 | Longo et al. |
| 2019/0285640 | A1 | 9/2019 | Longo |
| 2020/0029614 | A1 | 1/2020 | Longo et al. |
| 2021/0137149 | A1 | 5/2021 | Longo et al. |

FOREIGN PATENT DOCUMENTS

| | | |
|---|---|---|
| WO | 2004/023880 A1 | 3/2004 |
| WO | 2011/050302 | 4/2011 |
| WO | 2017/032739 A1 | 3/2017 |
| WO | 2017/212433 A1 | 12/2017 |

OTHER PUBLICATIONS

Choi, I.Y. et al., "A Diet Mimicking Fasting Promotes Regeneration and Reduces Autoimmunity and Multiple Sclerosis Symptoms," Cell Reports 15, Jun. 7, 2016, pp. 2136-2146.

Di Biase, S. et al., "Fasting-Mimicking Diet Reduces HO-1 to Promote T Cell-Mediated Tumor Cytotoxicity," Cancer Cell 30, Jul. 11, 2016, pp. 136-146.

Di Biase, S. et al., "Fasting regulates EGR1 and protects from glucose- and dexamethasone-dependent sensitization to chemotherapy," PLOS Biology, Mar. 30, 2017, pp. 1-21.

Guevara-Aguirre, J. et al., "Growth Hormone Receptor Deficiency is Associated with a Major Reduction in Pro-Aging Signaling, Cancer, and Diabetes in Humans," Aging, v. 3, issue 70, Feb. 16, 2011, 11 pgs.

Lee, C. et al., "Reduced Levels of IGF-I Mediate Differential Protection of Normal Cancer Cells in Response to Fasting and Improve Chemotherapeutic Index," Cancer Res., 70(4), Feb. 15, 2010, pp. 1564-1572.

Lee, C. et al., "Fasting Cycles Retard Growth of Tumors and Sensitize a Range of Cancer Cell Types to Chemotherapy," Cancer, v. 4, issue 124, Mar. 7, 2012, 12 pgs.

Levine, M.E. et al., "Low Protein Intake is Associated with a Major Reduction in IGF-1, Cancer and Overall Mortality in the 65 and Younger but Not Older Population," Cell Metabolism 19, Mar. 4, 2014, pp. 407-417.

Raffaghello, L. et al., "Starvation-dependent differential stress resistance protects normal but not cancer cells against high-dose chemotherapy," PNAS, v. 105, n. 24, Jun. 17, 2008, pp. 8215-8220.

Rangan, P. et al., "Fasting-Mimicking Diet Modulates Microbiota and Promotes Intestinal Regeneration to Reduce Inflammatory Bowel Disease Pathology," Cell Reports 26, Mar. 5, 2019, pp. 2704-2719.

Wei, M. et al., "Fasting-mimicking diet and markers/risk factors for aging, diabetes, cancer, and cardiovascular disease," Sci. Transl. Med. 9, Feb. 15, 2017, 13 pgs.

International Search Report and Written Opinion dated Jul. 2, 2019 for PCT/US2019/022488, 24 pgs.

Kohl, K. et al., Unique and shared responses of the gut microbiota to prolonged fasting: a comparative study across five classes of vertebrate hosts, FEMS Microbiology Ecology, v. 90, n. 3, 2014, pp. 883-894.

Schwab, C. et al., "Longitudinal study of murine microbiota activity and interactions with the host during acute inflammation and recovery," The ISME Journal, v. 8, n. 5, pp. 1101-1114.

Shiga, H. et al., "S1227 The Changes of Fecal Microbiota in Patients with Crohn's Disease During Elemental Diet," Gastroenterology, v. 134, n. 4, 2008, Abstract only, 1 pg.

Yeom, Y. et al., "Leaf extract regulates microbial dysbiosis by modulating the composition and diversity of the microbiota in destran sulfate sodium-induced colitis mice," BMC Complementary and Alternative Medicine, v. 16, n. 1, 2016, pp. 1-11.

Supplementary EP Search Report dated Nov. 17, 2021 for EP Appn. No. 19767587.9, 20 pgs.

Longo, V.D. et al., U.S. Appl. No. 17/009,382, filed Sep. 1, 2020, 71 pgs.

Mintel Foodis, Anonymous: "Foodis Pure Organic Baby Formula," GNPD (2004) 3 pages.

Farzaej, M.H. et al., "A mechanistic review of plant-derived natural compounds as dietary supplements for prevention of inflammatory bowel disease," Expert Review of Gastroenterology & Hepatology (2016), vol. 10, No. 6, pp. 745-758.

Van der Ark, K.C.H. et al., "Encapsulation of the therapeutic microbe Akkermansia Muciniphila in a double emulsion enhances survival in simulated gastric conditions," Food Research Int'l., 102 (2017), pp. 372-379.

Martinez-Herrero, S. et al., "Lack of Adrenomedullin Results in Microbiota Changes and Aggravates Azoxymethane and Dextran Sulfate Sodium-Induced Colitis in Mice," Frontiers in Physiology (2016), vol. 7, Article 595, 14 pages.

Maxwell, F.J. et al., "Isolation, growth on prebiotics and probiotic potential of novel bifidobacteria from pigs," Anaerobe 10 (2004), pp. 33-39.

Morais, R.M.S.C. et al., "Functional Dehydrated Foods for Health Preservation," J. of Food Quality, vol. 2018, Article ID 739636, (2018), 29 pages.

Nematgorgani, S. et al., "Effects of Urtica dioica leaft extract on inflammation, oxidative stress, ESR, blood cell count and quality of life in patients with inflammatory bowel disease," Journal of Herbal Medicine 9 (2017), pp. 32-41.

Otari, K.V. et al., "Protectiv effect of queous extract of *Spinacia Oleracea* leaves in experimental paradigms of inflammatory bowel disease," Inflammopharmacol (2012), 20, pp. 277-287.

Shiba, T. et al., "The Suppresive Effect of Bifidobacteria on Bacteroides Vulgatus, a Putative Pathogenic Microbe in Inflammatory Bowel Disease," Microbiol. Immunol., vol. 47(6), (2003), pp. 371-378.

Toumi, R. et al., "Probiotic Bacteria Lactobacillus and Bifidobacterium Attenuate Inflammation in Dextran Sulfate Sodium-Induced Experimental Colitis in Mice," Int'l J. of Immunopathology and Pharmacology, vol. 27, No. 4 (2014), pp. 615-627.

European Search Report for EP 19767587.9 dated Mar. 30, 2022, 44 pages.

\* cited by examiner

| Bacteria Family | C3 vs. F3 | F3 vs. C3 | C3 Approximate Fold Change Relative to F3 |
|---|---|---|---|
| S24-7 | | | +2.5 |
| Lactobacillaceae | ↓ | ↑ | -3 |
| Erysipelotrichaceae | ↓ | ↑ | -20 |
| Turicibacteraceae | ↑ | ↓ | +1.5 |
| Verrucomicrobiaceae | ↓ | ↑ | -2.5 |
| Lachnospiraceae | ↑ | ↓ | +2.5 |
| Ruminococcaceae | ↑ | ↓ | +4 |
| Bifidobacteriaceae | ↓ | ↑ | -77 |

Fig. 1C

| Enriched Genus/Species/Strains in F3 | | | |
|---|---|---|---|
| Family | Genus | Species | Strain |
| Lactobacillaceae | Lactobacillus | -- | -- |
| Erysipelotrichaceae | Allobaculum | -- | -- |
| Bacteroidaceae | Bacteroides | acidifaciens | Bacteroides acidifaciens |
| Bifidobacteriaceae | Bifidobacterium | choerinum | Bifidobacterium choerinum |

Fig. 1D

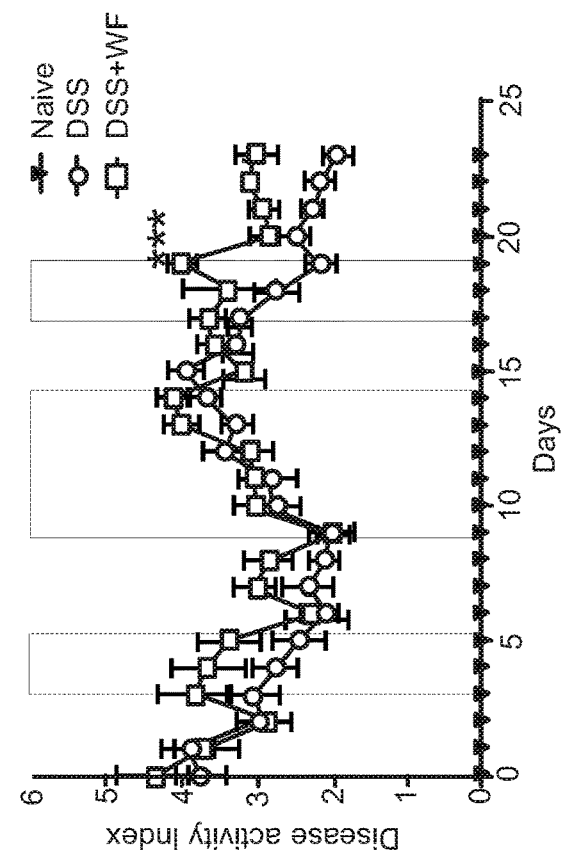
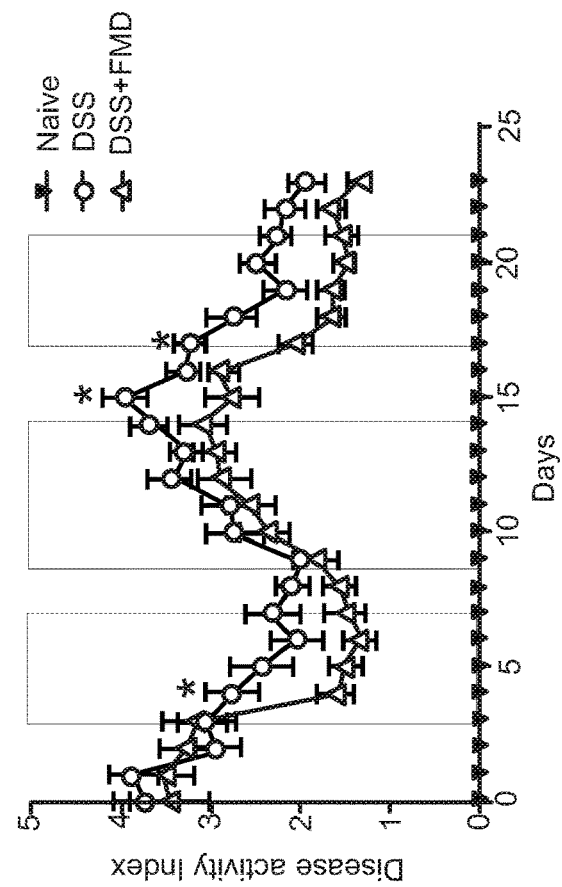
Fig. 3A
Fig. 3B

Top 8 most abundant families between the DSS+FMD group 9 days after the fie DSS cycle/two days after the 2s FMD cycle, and the DSS+WF group 9 days after the 4n DSS cycle/two days after the 2nd water-only fast.

| Family | DSS + FMD Mean (sd) | DSS + WF Mean (sd) |
| --- | --- | --- |
| S24-7 | 27.5 (7.9) | 34.5 (6.72) |
| Lactobacillaceae | 45.2 (4.2) | 25.8 (3.97) |
| Erysipelotrichaceae | 10.5 (5.71) | 0.286 (0.184) |
| Turicibacteraeae | 2.84 (3.63) | 2.17 (2.59) |
| Verrucomicrobiaceae | 3.85 (2.88) | 3.5 (1.05) |
| Lachnospiraceae | 1.16 (0.756) | 5.42 (3.32) |
| Ruminococcaceae | 0.568 (0.308) | 4.81 (3.09) |
| Bifidobacteriaceae[a] | 2.67 (3.56) | -- |
| [Paraprevotellaceae][b] | -- | 6.13 (0.148) |

[a]Not ranked in top 8 most abundant families for DSS+WF groups.

[b]Not ranked in top 8 most abundant families for DSS+FMD group

*Fig. 7B*

FASTING-MIMICKING DIET (FMD) BUT NOT WATER-ONLY FASTING PROMOTES REVERSAL OF INFLAMMATION AND IBD PATHOLOGY

CROSS-REFERENCE TO RELATED APPLICATIONS

This application is the U.S. national phase of PCT Appln, No, PCT/US2019, 022488 filed Mar. 15, 2019 which claims the benefit of U.S. provisional patent application Ser. Nos. 62/643,296 filed Mar. 15, 2018; 62/734,475 filed Sep. 21, 2018; and 62/735,147 filed Sep. 23, 2018, the disclosures of which are hereby incorporated in their entirety by reference herein.

TECHNICAL FIELD

In at least one aspect, the present invention provides a treatment for gastrointestinal autoimmune/inflammatory disease by mediating positive changes in the gut microbiome. The present invention combines the composition of a fasting-mimicking diet (FMD) with the regimen of a FMD plus refeeding cycles to enhance the cultivation and expansion of beneficial gut microbiota. In another aspect, the composition of microbiota which can alone promote therapeutic effects against gastrointestinal inflammatory diseases is described. Additionally, FMD plus refeeding cycles promoted the enhanced reversal of IBD pathology in comparison to 48 hr water-only fasting cycles.

BACKGROUND

Autoimmune diseases involve a miscommunication between innate and adaptive immunity and an imbalance between T lymphocytes populations, which play critical roles in the immuno-pathogenesis of many autoimmune/chronic inflammatory diseases[1-3]. It has been shown that both hyperactive innate immune response (i.e. macrophages and dendritic cells), imbalance between autoreactive associated effector cells (i.e. CD4$^+$Th1 and CD4$^+$Th17) and anti-inflammatory associated regulatory T cells (CD4$^+$ Treg), and pro-inflammatory cytokine productions contribute to the pathogenesis of major gastrointestinal autoimmune/inflammatory diseases including Crohn's disease (CD), ulcerative colitis (UC), irritable bowel syndrome, celiac disease, microscopic colitis (collagenous and lymphocytic colitis), and Bejcet disease[3-8].

Microbiome and probiotic-based therapies for gastrointestinal autoimmune/inflammatory diseases currently under investigation primarily involve approaches that include fecal microbiota transplantation (FMT), oral probiotic administration, or changes in diet[9]. While these approaches show promise, there is a need for fine-tuning these therapies so they are suitable for treating patients affected by gastrointestinal autoimmune/inflammatory diseases clinically[10].

SUMMARY

The present invention solves one or more problems of the prior art by providing a method for treating or preventing autoimmune and/or inflammatory disease. The method includes a step of identifying a subject exhibiting symptoms of or at risk for autoimmune and/or inflammatory disease administering a periodic fasting mimicking diet.

In another embodiment, a probiotic composition for gastrointestinal autoimmune and/or inflammatory disease is provided. The probiotic composition includes a bacterial component selected from the group consisting of *Lactobacillaceae, Erysipelotrichaceae*, and *Bifidobacteriaceae* with the option of adding other beneficial microbial populations identified in the experiments set forth below, and combinations thereof to be administered for the prevention and treatment for gastrointestinal autoimmune and/or inflammatory disease. The probiotic composition also includes an optional protective component that stabilizes the bacterial component.

The fasting-mimicking diet is also shown to enhance the reversal of IBD pathology in comparison to 48 hr water-only fasting cycles, as seen by improvement in disease activity level, colon and small intestine regeneration, an increase in intestinal regeneration markers, and shifts in the microbiome that promote the sustained expansion of probiotic strains.

In another embodiment, a dietary supplement for the prevention and treatment of gastrointestinal autoimmune and/or inflammatory disease is provided. The dietary supplement include pre-biotic ingredients and/or vegetables having such pre-biotic ingredients.

BRIEF DESCRIPTION OF THE DRAWINGS

FIG. 1C provides a table comparing population sizes of the top 8 microbiota families between the C3 and F3 time points. (C3=9 days after 4th DSS Cycle, F3=2 days after 2nd FMD cycle and 9 days after 4th DSS cycle), as well as approximate fold change of the populations at C3 vs. F3.

FIG. 1D provides a Table outlining the most enriched gut microbiota in the F3 group at the genus, species, and strain levels.

FIG. 3A provides a scatter plot of the Disease Activity Index (DAI) scores of the Naive (n=15), DSS control diet, and DSS control diet plus 2 cycles of FMD (DSS+FMD) starting after the third DSS cycle.

FIG. 3B provides a plot of the Disease Activity Index (DAI) scores of the Naive (n=15), DSS control diet, and DSS control diet plus 2 cycles of water-only fasting (DSS+WF) groups starting after the third DSS cycle.

FIG. 7B provides table summarizing the top 8 most abundant families in fecal samples between the groups at these timepoints.

DETAILED DESCRIPTION

Figure 1A:
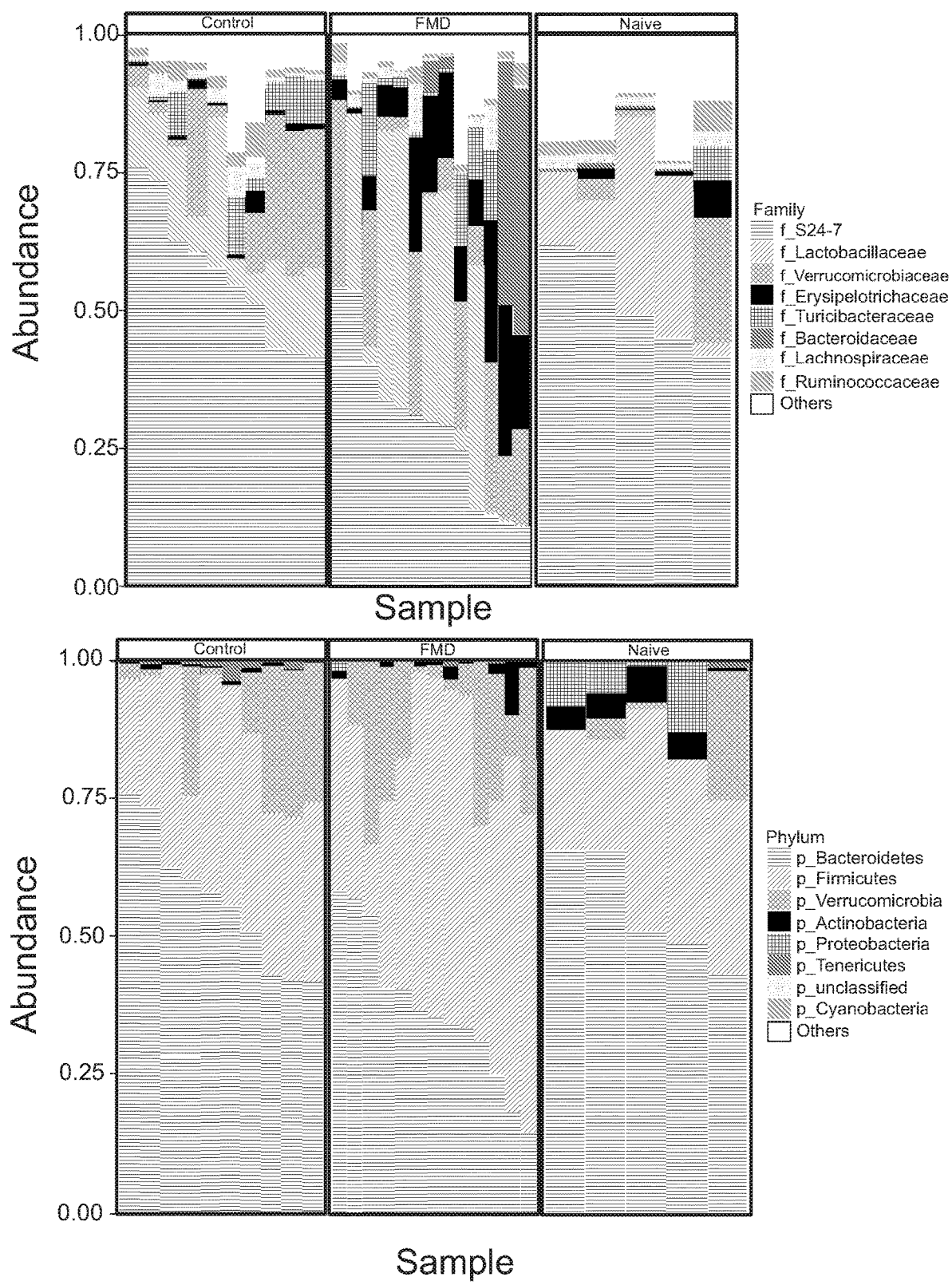
FIG. 1A provides plot showing the most abundant taxa at the phylum and family level.

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Abbreviations:

"CRP" means c-reactive protein.

"DAI" means disease activity index.

"DSS" means dextran sulfate sodium.

"FMD" means fasting mimicking diet.

"FMT" means fecal microbiota transplant.

"FT" means fecal transplant.

"IBD" means Inflammatory bowel disease.

"WF" means water-only fasting.

The term "subject" refers to a human or animal, including all mammals such as primates (particularly higher primates), sheep, dog, rodents (e.g., mouse or rat), guinea pig, goat, pig, cat, rabbit, and cow.

The term "fasting mimicking and enhancing diet" means a diet that mimics the effects of fasting typically by providing a subject with at most 50-75% of their normal caloric intake. However, if the fasting mimicking diet composition is maintained, based on our current and previous findings, partial disease prevention and treatment effects are anticipated even if 100% of the normal caloric intake is provided to subjects. The term "fasting mimicking and enhancing diet" is sometimes simply referred to as a "fasting mimicking diet." These diets include those diets that have been referred to as fasting mimicking diets. Examples of useful fasting mimicking and enhancing diets and method for monitoring the effects of these diets on markers such as IGF-1 and IGFBP1 in the context of the present invention are set forth in U.S. patent application Ser. Nos. 14/273,946 filed May 9, 2014; 14/497,752 filed Sep. 26, 2014; 12/910,508 filed Oct. 22, 2010; 13/643,673 filed Oct. 26, 2012; 13/982,307 filed Jul. 29, 2013; 14/060,494 filed Oct. 22, 2013; 14/178,953 filed Feb. 12, 2014; 14/320,996 filed Jul. 1, 2014; 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful in the present invention.

The term "prebiotic" refers to food ingredients that promote the growth of beneficial microorganism in a subject's intestines. Typically, the food ingredients are nondigestible food ingredients.

The term "probiotic" refers a substance or composition stimulates the growth of beneficial microorganisms, and in particular, growth of beneficial microorganism in a subject's intestines.

In an embodiment, a method for treating or preventing an autoimmune and/or inflammatory disease is provided. Examples of these conditions includes Crohn's disease (CD), ulcerative colitis (UC), irritable bowel syndrome, celiac disease, microscopic colitis (collagenous and lymphocytic colitis), and Bejcet disease. The method includes a step of identifying a subject exhibiting symptoms of autoimmune and/or inflammatory disease administering a fasting mimicking diet. Identification of these conditions can involve blood test, barium x-rays, colonoscopy with or without biopsy, and the like. In a refinement, the fasting mimicking diet is administered for 2 or more cycles.

The FMD is administered to the subject for a first predetermined time period. In some variations, the first predetermined time period is equal to or greater than, in increasing order of preference, 3, 5, 6, or 7 days. In addition, the first predetermined time period is equal to or less than, in increasing order of preference, 20, 15, 10, or 8 days. In a refinement, the first predetermined time period is 1, 2, 3, 4, 5, 6, 7, 8, 9, or 10 days. In another refinement, the first predetermined time period is 5 to 10 days. In some variations of the methods set forth herein, the fasting mimicking and enhancing diet is repeated at intervals. For example, the fasting mimicking and enhancing diet can be initiated once a month for the duration of the subject's treatment which can be 3 months to a year or more (e.g., 1 to 5 years).

In some variations, the fasting mimicking diet for each of the methods set forth herein provides at most, in increasing order of preference, 50%, 40%, 30%, or 100% of the subject's normal caloric intake. In a refinement, the fasting mimicking diet provides at least, in increasing order of preference, 5%, 10%, or 20% of the subject's normal caloric intake. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the fasting mimicking diet provides the subject with from 700 to 1200 kcal/day. In a particularly useful refinement, the fasting mimicking diet provides a male subject of average weight with at most 1100 kcal/day and a female subject of average weight with at most 900 kcal/day. In some refinements, the fasting mimicking diet provides at most, in increasing order of preference, 1500 kcal/day, 1400 kcal/day, 1300 kcal/day, 1200 kcal/day, 1100 kcal/day, 1000 kcal/day, 900 kcal/day, 800 kcal/day, 700 kcal/day, 600 kcal/day, 500 kcal/day, or 2500 kcal/day. In some further refinements, the fasting mimicking diet provides at least, in increasing order of preference, 0 kcal/day, 10 kcal/day, 100 kcal/day, 200 kcal/day, 300 kcal/day, 400 kcal/day, or 500 kcal/day.

In certain variations, the fasting mimicking and enhancing diet provides from 4.5 to 7 kilocalories per pound of subject for a first day (day 1) and then 3 to 5 kilocalories per pound of subject per day for the second to the final day. Day 1 ingredients are a blend of beets, carrots, collard, spinach, kale, mushroom, tomato, extra virgin olive oil, essential fatty acids, chicken broth, and veggie broth, while Day 2-4 is restricted to chicken broth, veggie broth, and glycerol. The composition of the Day 1 FMD is approximately 25% of a blend of the vegetables listed above, 60% extra virgin olive oil and essential fatty acids, and 10% of the broth mix. After a cycle of the fasting mimicking and enhancing diet, a second diet is administered to the subject for a second predetermined time period. In a refinement, the second diet provides an overall calorie consumption that is within 20 percent of a subject's normal calorie consumption for 10 to 26 days (e.g., immediately) following the fasting mimicking and enhancing diet.

Notably, the relative protein, carbohydrate and fat content of the FMD can be varied to achieve similar results based on total calorie intake and length. This can be assessed based on IGF-1, IGFBP1, glucose and ketone bodies. For example, a diet lasting 1 week and containing a relatively high level of protein and carbohydrates but providing 10-20% of the normal calorie intake can have similar fasting mimicking properties to a diet lasting 5 days but containing low levels of carbs and proteins and providing 50% of normal calories. In other words, this application describes fasting mimicking properties that provide beneficial effects which are variable based on relative macronutrient composition, diet length and calorie intake. The formulations provided above are examples based on the discoveries made here and previously which do not include all of the fasting mimicking compositions and methods which are obvious to one skilled in the art to achieve the required IGF-1, IGFBP1, ketone bodies, and glucose levels achieved by the FMDs described here.

Additional examples of useful fasting mimicking and enhancing diets in the context of the present invention are set forth in U.S. patent application Ser. Nos. 14/273,946 filed May 9, 2014; 14/497,752 filed Sep. 26, 2014; 12/910,508 filed Oct. 22, 2010; 13/643,673 filed Oct. 26, 2012; 13/982, 307 filed Jul. 29, 2013; 14/060,494 filed Oct. 22, 2013; 14/178,953 filed Feb. 12, 2014; 14/320,996 filed Jul. 1, 2014; 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful in the present invention. Additional examples of FMD diets are found in U.S. patent application Ser. No. 15/148,251 and WIPO Pub. No. WO2011/050,302 and WIPO Pub. No. WO2011/050,302; the entire disclosures of which are hereby incorporated by reference and attached as exhibits A-H. Details of a particularly useful diet, the PROLON diet are found in U.S. patent application Ser. No. 15/432,803 filed Feb. 14; the entire disclosure of which is hereby incorporated by reference.

Figure 1B:
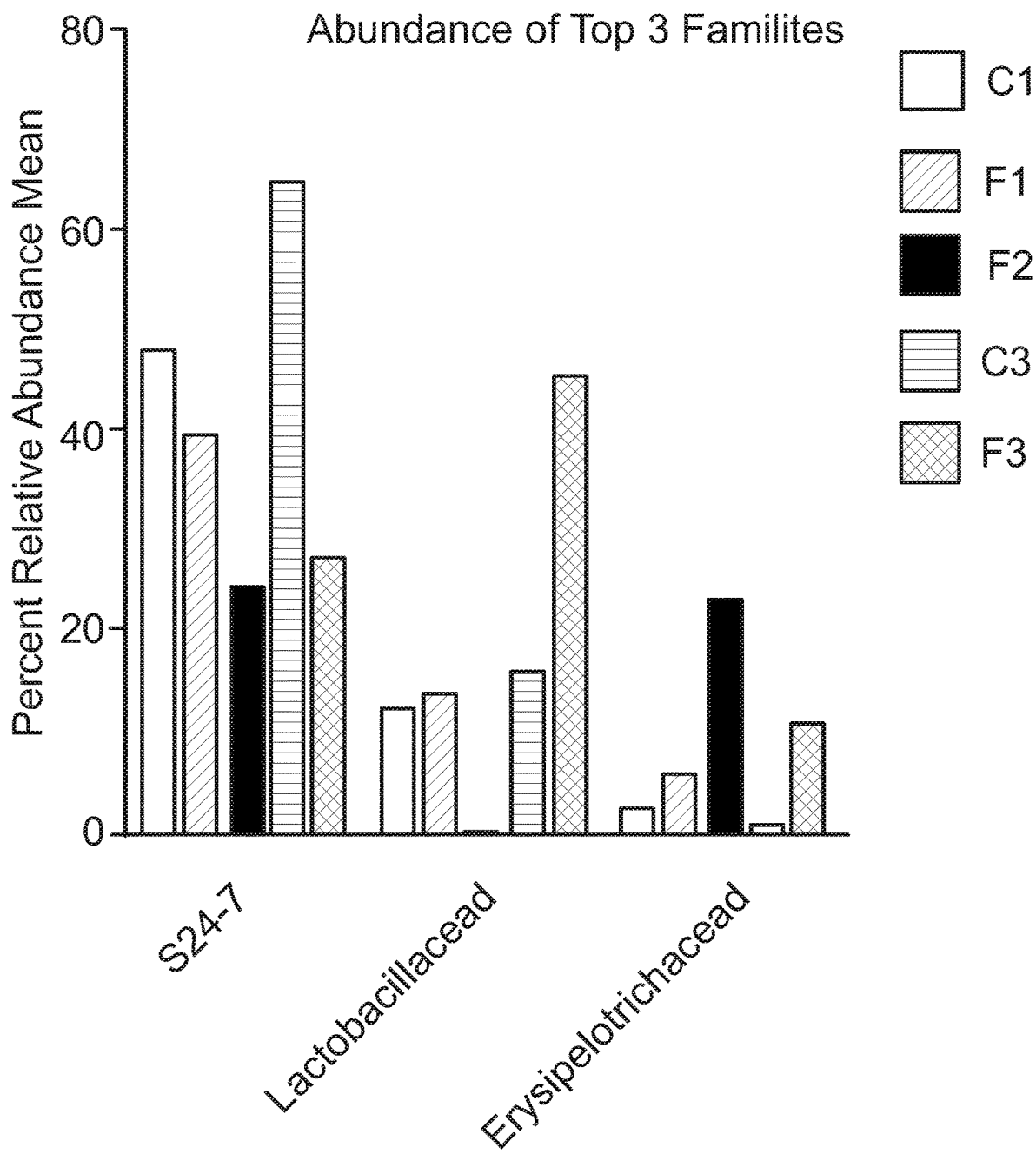
FIG. 1B provides a graphical representation of the top 3 microbiota families (S24-7, *Lactobacillaceae, Erysipelotrichaceae*) and their percent relative abundance mean at specific timepoints of diet administration (C1=2 days after 4th DSS Cycle, F1=after completing one FMD cycle and 2 Days after 4th DSS cycle, F2=after completing four days of 2nd FMD cycle, C3=9 days after 4th DSS Cycle, F3=2 days after 2nd FMD cycle and 9 days after 4th DSS cycle).

In a variation, it was found that two cycles of FMD, followed by two days of refeeding (with the subjects normal diet), increased a combination of gut microbiota at the family level (*Lactobacillaceae, Erysipelotrichaceae, Verrucomicrobiaceae,* and *Bifidobacteriaceae*) while decreasing others (S24-7, *Turicibacteraceae, Lachnospiraceae,* and *Ruminococcaceae*) when compared to the gut microbiota composition induced by a control diet (FIG. 1A-C). Within the families *Lactobacillaceae, Erysipelotrichaceae,* and *Bifidobacteriaceae,* the genera *Lactobacillus, Allobaculum,* and *Bifidobacterium* were enriched, respectively, after two cycles of FMD followed by two days of refeeding. At the microbial strain level, *Bacteroides acidifaciens* and *Bifidobacterium choerinum* were uniquely enriched in this group (FIG. 1D), both of which have been noted to prevent obesity and display probiotic activity to treat intestinal disorders, respectively[11,12].

In another embodiment, a probiotic composition for gastrointestinal autoimmune and/or inflammatory disease is provided. The probiotic composition includes a bacterial component selected from the microbial strains consisting of *Bacteroides acidifaciens* and *Bifidobacterium choerinum,* and combinations thereof to be administered for the prevention and treatment for gastrointestinal autoimmune and/or inflammatory disease. The probiotic composition can also include an optional protective component that stabilizes the bacterial component. In a variation, the probiotic composition further includes gut microbiota strains isolated from the genera *Lactobacillus, Allobaculum,* and *Bifidobacterium.* In another variation, the bacterial component includes a combination of *Bacteroides acidifaciens* and *Bifidobacterium choerinum* such that the *Bifidobacterium choerinum* enhances the probiotic activity of *Bacteroides acidifaciens* and/or *Bacteroides acidifaciens* enhances the probiotic activity of *Bifidobacterium choerinum.* The probiotic composition can be administered to a patient in an effective amount to relieve symptoms of gastrointestinal autoimmune and/or inflammatory disease with or without an FMD.

In a variation, the probiotic composition of the invention includes at least $10^3$ CFU/g of each of *Bacteroides acidifaciens, Bifidobacterium choerinum,* and optionally the strains isolated from the genera *Lactobacillus, Allobaculum,* and *Bifidobacterium* in a capsule. The bacterial species therefore are present in the dose form as live bacteria, whether in dried, lyophilized, or sporulated form. For example, the dose form can be a capsule containing the bacterial components in a dried form, blended with a suitable carrier. A typical probiotic composition will include from about $10^3$ to about $10^{14}$ CFU/g of each bacterial component. In a refinement, the probiotic composition includes $10^5$-$10^{12}$ CFU/g of each bacterial component. In another refinement, the probiotic composition includes $10^9$-$10^{13}$ colony forming units/g of each bacterial component. In another refinement, the probiotic composition includes $10^5$-$10^7$ CFU/g of each bacterial component. In still another refinement, the probiotic composition includes $10^8$-$10^9$ CFU/g.

As set forth above, examples of protective components and methods for stabilizing probiotics such as the probiotic composition of the present invention is found in *Different Methods of Probiotics Stabilization,* Kamila Goderska, Oct. 3, 2012 DOI: 10.5772/50313; the entire disclosure of which is hereby incorporated by reference. In a variation, the protect component can be a protective carrier and/or protective coating and/or a protective encapsulant. In a refinement, the protective carrier is a liquid at 25° C. (i.e., liquid carrier) with the bacterial component dispersed therein. Examples of such liquids include hydroxylated hydrocarbon carriers such as polyol (e.g., glycerol). In a variation, these liquids interact with the bacterial component thereby forming a modified bacterial component. Such interactions can include chemical bonding (e.g., hydrogen bonding and Van der Waals bonds). Moreover, the liquid carrier can adsorb (e.g., including adsorption) to the bacteria cell wall and/or cell membrane.

In a variation, the protective component includes a stabilization agent (e.g., a compound) that interacts (e.g., chemical bonding, adsorbing, and adsorption). with or encapsulates the bacterial component. Examples of such compounds include, but are not limited to, adonitol, betaine, carbohydrates (e.g., sugars), proteins, amino acids, mixtures of sugar and protein (e.g., protectans), gums and skim milk. In this regard, protein can form relatively stable intracellular glasses. In a refinement, the stabilization agent is dissolved or dispersed in a room temperature liquid. Finally, the liquid carrier, the protective compound, or the protective coating can be contained in the interior of the bacteria (e.g., by diffusion or ingestion).

In another variation the protective component is an protect encapsulant. The bacterial component can be encapsulated by spray drying, fluidized bed drying and vacuum drying. In a refinement, the protective component includes an encapsulating agent selected from the group consisting of maltodextrins, skim milk, reconstituted skim milk, casein, soybean protein, trehalose, maltodextrin, and combinations thereof. In a further refinement, the protective component includes a prebiotic such as inulin, oligofructose, and oligofructose-enriched inulin The bacterial compositions of the invention may additionally and optionally include an optional additive selected from any suitable adjuvants, excipients, additives, additional carriers, additional therapeutic agents, bioavailability enhancers, side-effect suppressing components, diluents, buffers, flavoring agents, binders, preservatives or other ingredients and combinations thereof that do not preclude the efficacy of the composition. In a refinement, the bacterial compositions are present in an amount from about 50% to about 90% by weight of the composition and 10% to 50 weight percent of an optional additive.

In a variation, the probiotic composition can be administered along the method for preventing or treating gastrointestinal autoimmune and/or inflammatory disease set forth above. In this regard, the probiotic composition can be administered on each day or any subset of days that the FMD diet is administered. In a refinement, the probiotic composition can be administered on any day on which the FMD diet is not administered.

In another embodiment, a dietary supplement for the prevention and treatment of gastrointestinal autoimmune and/or inflammatory disease is provided. The dietary supplement include pre-biotic ingredients or vegetable having such pre-biotic ingredients. Table 1 provides the prebiotic components found in several vegetables. In a refinement, the dietary supplement includes a vegetable mixture of beets, carrots, collard, spinach, kale, mushroom, tomato, and optionally nettle leaf. In a refinement, the vegetable mixture can also include extra virgin olive oil, essential fatty acids, and/or vegetable broth. Typically, the vegetable mixture incudes 5 to 20 weight percent beets, 5 to 20 weight percent carrots, 5 to 20 weight percent collard, 5 to 20 weight percent spinach, 5 to 20 weight percent kale, 5 to 20 weight percent mushroom, 5 to 20 weight percent tomato, and 0 to 20 weight percent nettle leaf. In a refinement, the , the vegetable mixture incudes 8 to 15 weight percent beets, 8 to 15 weight percent carrots, 8 to 15 weight percent collard, 8 to 15 weight percent spinach, 8 to 15 weight percent kale, 8 to 15 weight percent mushroom, 8 to 15 weight percent tomato, and 5 to 15 weight percent nettle leaf.

In a refinement, the vegetable mixture is a powdered vegetable mixture that is formed by desiccating (e.g., drying) the vegetable components and grinding or mechanically manipulating into a powder to form a dried vegetable powder. In a variation, the order of these steps can be interchanged (e.g., grinding and then drying). It should be appreciated that the drying should be performed without heating to preserve vitamin content. Examples of desiccating the vegetable mixture includes freeze-drying, convection drying, spray drying, and the like. In a refinement, the dried vegetable powder has a plurality of particles with a size (e.g., diameter or largest spatial dimension) in the range of 1 to 10 microns. In a further refinement, the dried vegetable powder has an average size (e.g., diameter or largest spatial dimension) in the range of 1 to 10 microns. Of course, particles of this size range have altered material properties (e.g., absorption properties, ingestability, and the like) as compared to the naturally occurring vegetables. Consistent with the ranges set forth above, the dried vegetable powder incudes 5 to 20 weight percent of powder formed from beets, 5 to 20 weight percent of powder formed from carrots, 5 to 20 weight percent collard, 5 to 20 weight percent of powder formed from spinach, 5 to 20 weight percent of powder formed from kale, 5 to 20 weight percent mushroom, 5 to 20 weight percent of powder formed from tomato, and 0 to 20 weight percent of powder formed from nettle leaf. In a refinement, the , the vegetable mixture incudes 8 to 15 weight percent of powder formed from beets, 8 to 15 weight percent of powder formed from carrots, 8 to 15 weight percent of powder formed from collard, 8 to 15 weight percent of powder formed from spinach, 8 to 15 weight percent of powder formed from kale, 8 to 15 weight percent of powder formed from mushroom, 8 to 15 weight percent of powder formed from tomato, and 5 to 15 weight percent of powder formed from nettle leaf. A useful batch of the diet supplement will provide a dry powder equivalent of 5 servings of vegetables (powder equivalent to 375 grams of raw vegetables, total). Typically, the dietary supplement is combined with water and optionally heated to be consumed as a broth.

In a refinement, the dietary supplement is administered to a subject several times a week. The subject may have been identified as having IBD and/or gastrointestinal autoimmune and/or inflammatory disease. In a further refinement, the dietary supplement can be administered 1, 2, 3, 4, 5, 6, or 7 days a week. In still a further refinement, the dietary supplement can be taken twice as part of a week as part of a protocol against autoimmunities (e.g., once at day 1 and once in day 4 of any diet such as the FMD set forth above). In this regard, the dietary supplement can be combined with the probiotic composition and/or the method for preventing or treating gastrointestinal autoimmune and/or inflammatory disease set forth above.

TABLE 1

Prebiotic components of several vegetables.

| Vegetable | Prebiotic Ingredients |
| --- | --- |
| Beet Root | Cellulose, pectin/Pectic polysaccharides |
| Carrot Root | Arabinogalactans |
| Collard Leaf | Soluble fibers, glycosylates |
| Kale Leaf | Soluble fibers, glucosinolates |
| Nettle Leaf | Terpenoids, carotenoids, chlorophyll, vitamins, tannins, carbohydrates, sterols, polysaccharides, isolectins, polyphenols, oleanol acid, sterols and steryl glycosides |
| Spinach Leaf | Hydroxycinnamic acids: (E)-ferulic acid and (E)-p-coumaric acid; pectic polysaccharides |
| Tomato Fruit | Arabinogalactans, oligofructose |
| Maitake Mycelium | Polysaccharides: starch, natural oligofructoses, fructo-oligosacharides (FOS), lactulose, and galactomannan |

The following examples illustrate the various embodiments of the present invention. Those skilled in the art will recognize many variations that are within the spirit of the present invention and scope of the claims.

An FMD was administered in mice displaying signs for gastrointestinal autoimmune and/or inflammatory disease to further confirm that this combination of FMD gut microbiota executes positive changes on IBD-associated phenotypes (see, FIGS. 1 and 2).

The experimental mouse FMD is based on a nutritional screen that identified ingredients which allow high nourishment during periods of low-calorie consumption, modeled after the same ingredients used in the human version of the FMD. The FMD diet consists of two different components designated as day 1 diet and day 2-4 diet that were fed in this order respectively. Day 1 ingredients are a blend of beets, carrots, collard, spinach, kale, mushroom, tomato, extra virgin olive oil, essential fatty acids, chicken broth, and veggie broth, while Day 2-4 is restricted to chicken broth, veggie broth, and glycerol. Day 1 diet contains 7.87 kJ/g, the day 2-4 diet is identical on all feeding days and contains 1.51 kJ/g. Day 1 and day 2-4 diets were supplied to the FMD cohort with the average intake of the ad lib control group (~4 g) every two weeks. On average, mice consumed 11.07 kJ (plant-based protein 0.75 kJ, carbohydrate 5.32 kJ, fat 5 kJ) on each day of the FMD regimen. Mice consumed all the supplied food on each day of the FMD regimen and showed no signs of food aversion.

FIG. 1 shows that two, 4-day FMD cycles induces changes in gut microbiota at the phylum and family level. FIG. 1A provides plots showing the most abundant taxa at the phylum and family level while FIG. 1B provide a bar chart of the top 3 microbiota families (S24-7, Lactobacillaceae, Erysipelotrichaceae) and their percent relative abundance mean at specific timepoints of diet administration (C1=2 days after 4th DSS Cycle, F1=after completing one FMD cycle and 2 Days after 4th DSS cycle, F2=after completing four days of 2nd FMD cycle, C3=9 days after 4th DSS Cycle, F3=2 days after 2nd FMD cycle and 9 days after 4th DSS cycle). (C) Table comparing population sizes of the top 8 microbiota families between the C3 and F3 time points. (C3=9 days after 4th DSS Cycle, F3=2 days after 2nd FMD cycle and 9 days after 4th DSS cycle), as well as approximate fold change of the populations at C3 vs. F3.

FIG. 1D provides a table outlining the most enriched gut microbiota in the F3 group at the genus, species, and strain levels.

Figure 2A:
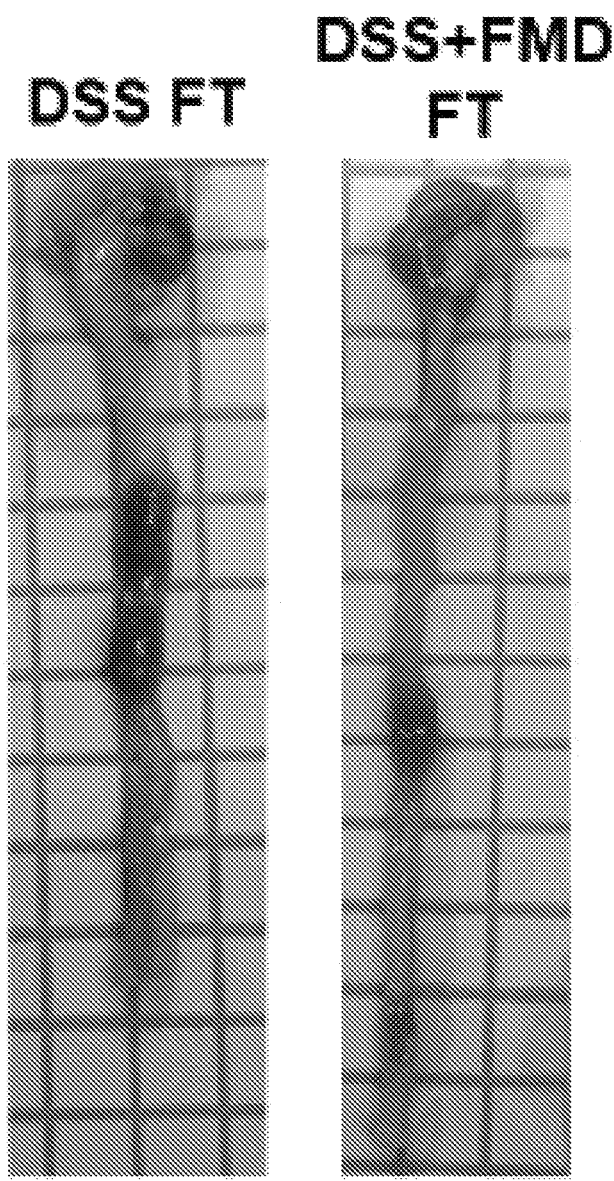
FIG. 2A provides a visual representation of colon lengths of fecal transplant (FT) recipients. Recipients were either given an FMT from DSS control or DSS+FMD donors.
Figure 2B:
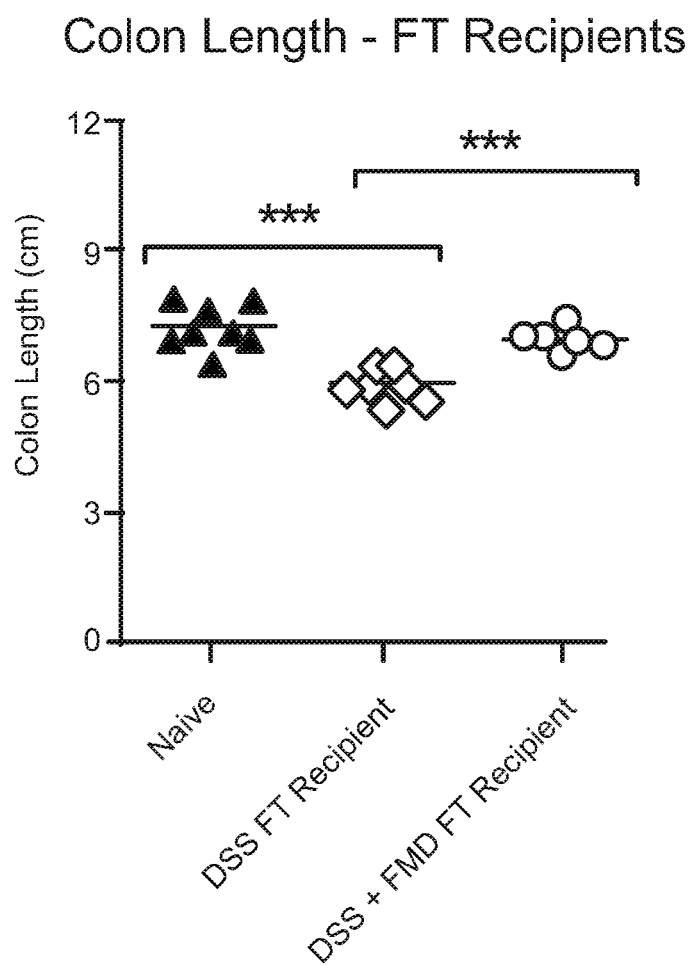
FIG. 2B provides colon length quantification among Naive, DSS FT Recipients, and DSS+FMD Recipients (One-way ANOVA, ***p<0.001).
Figure 2C:
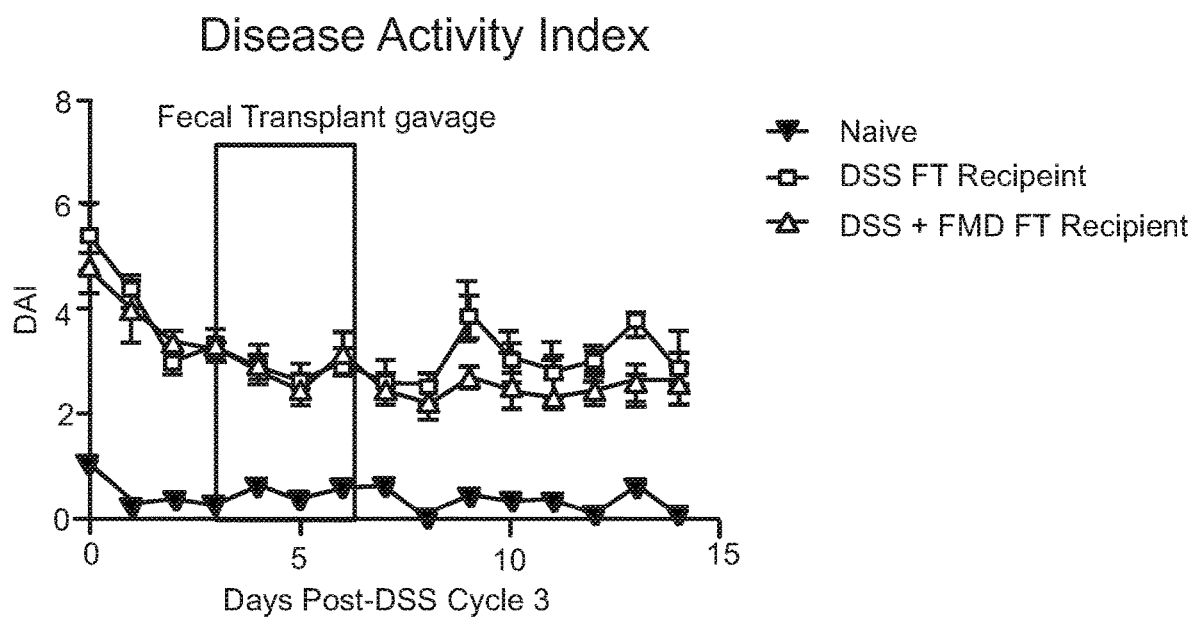
FIG. 2C provide a plot of Overall Disease Activity Index (DAI) quantification after the 3rd cycle of DSS and through the fecal transplant administration period.
Figure 2D:
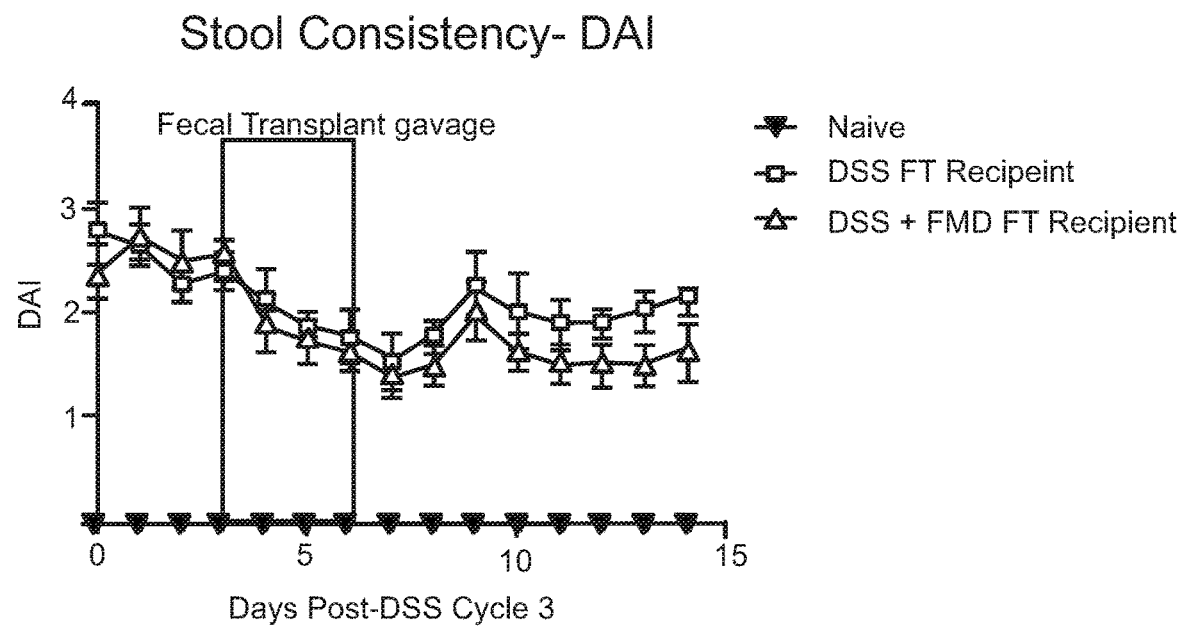
FIG. 2D provides a scatter plot of stool consistency after the 3rd cycle of DSS and through the fecal transplant administration period.

FIGS. 2A-C provides results of a fecal microbiota transplant (FMT) derived from mice fed with a human FMD diet induces changes in mouse colon length and improved disease outcome. FIG. 2A provide a visual representation (i.e., a photograph) showing colon lengths of fecal transplant (FT) recipients. Recipients were either given an FMT from DSS control or DSS+FMD donors. DSS causes a (DSS)-induced colitis model that is commonly used to study IBD in mice.[13,14] DSS is a sulfated polysaccharide that is especially toxic to the colonic epithelium. FIG. 2B provides colon length quantification among Naive, DSS FT Recipients, and DSS+FMD Recipients (One-way ANOVA, ***p<0.001). FIGS. 2C and 2D provide overall Disease Activity Index (DAI) quantification and stool consistency after the 3rd cycle of DSS and through the fecal transplant administration period.

Figure 3D:
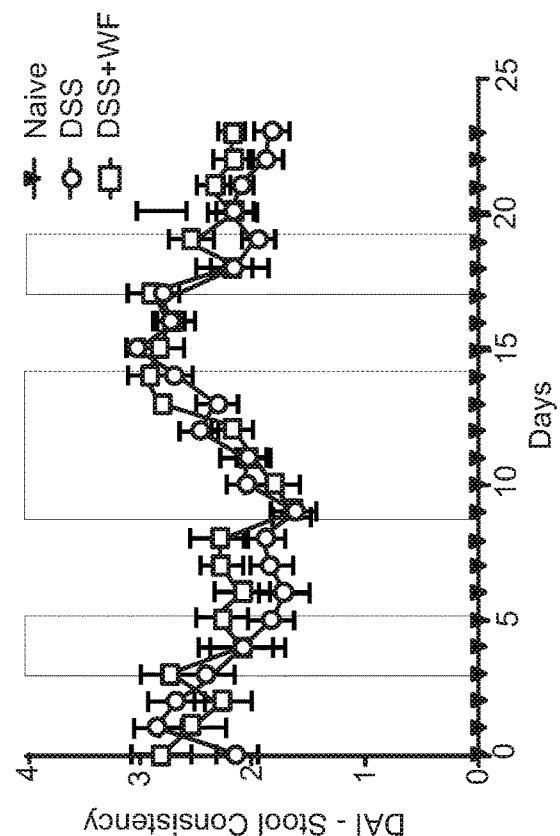
FIG. 3D provides a plot of the stool consistency variable of the Disease Activity Index (DAI) scores of the Naïve, and DSS control diet plus 2 cycles of water-only fasting groups starting after the third DSS cycle.
Figure 3C:
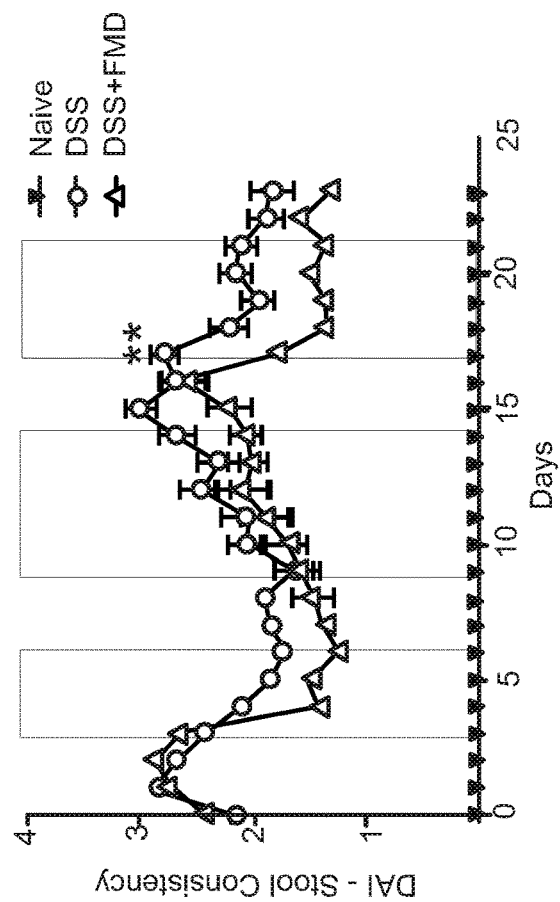
FIG. 3C provides a plot of the stool consistency variable of the Disease Activity Index (DAI) scores of the Naive, DSS control diet, DSS control diet plus 2 cycles of FMD.
Figure 3F:
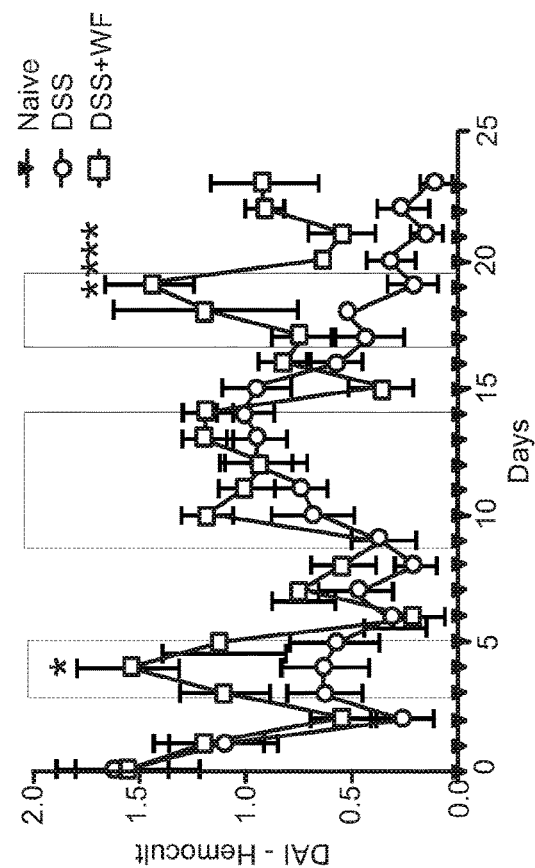
FIG. 3F provides a plot of the Hemoccult test variable of the Disease Activity Index (DAI) scores of the Naïve, DSS control diet, and DSS control diet plus 2 cycles of water-only fasting groups starting after the third DSS cycle.
Figure 3E:
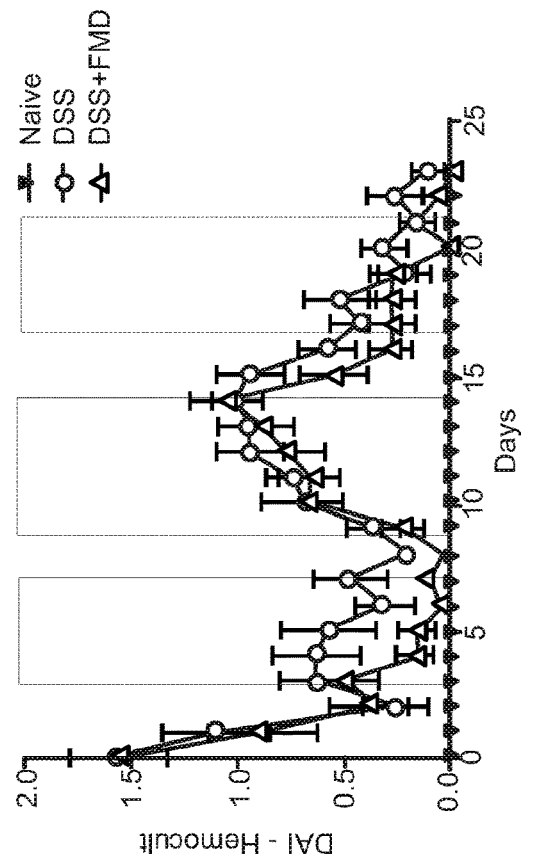
FIG. 3E provides a plot of the Hemoccult test variable of the Disease Activity Index (DAI) scores of the Naïve, DSS control diet, and DSS control diet plus 2 cycles of FMD.

FIGS. 3A-C provide experimental comparison of disease activity in mice treated with 4 DSS cycles, and either 2 FMD cycles or 2 water-only fasting cycles. Mice treated with FMD cycles have improvement in disease activity, firmer stools (lower score for stool consistency), and less presence of blood in stools (lower score for Hemoccult) in comparison to mice treated with 48 hr water-only fasting cycles FIGS. 3A and 3B provide plots of the Disease Activity Index (DAI) scores of the Naive (n=15), DSS control diet, and DSS control diet plus 2 cycles of FMD (DSS+FMD) or DSS control diet plus 2 cycles of water-only fasting (DSS+WF) groups starting after the third DSS cycle. FIGS. 3C and 3D provide plots of the stool consistency variable of the Disease Activity Index (DAI) scores of the Naïve, DSS control diet, DSS control diet plus 2 cycles of FMD, and DSS control diet plus 2 cycles of water-only fasting groups starting after the third DSS cycle. FIGS. 3E and 3F provide the Hemoccult test variable of the Disease Activity Index (DAI) scores of the Naïve, DSS control diet, DSS control diet plus 2 cycles of FMD, and DSS control diet plus 2 cycles of water-only fasting groups starting after the third DSS cycle. (Two-way ANOVA, *p<0.05, p<0.01, *p<0.001, ****p<0.0001).

Figure 4A:
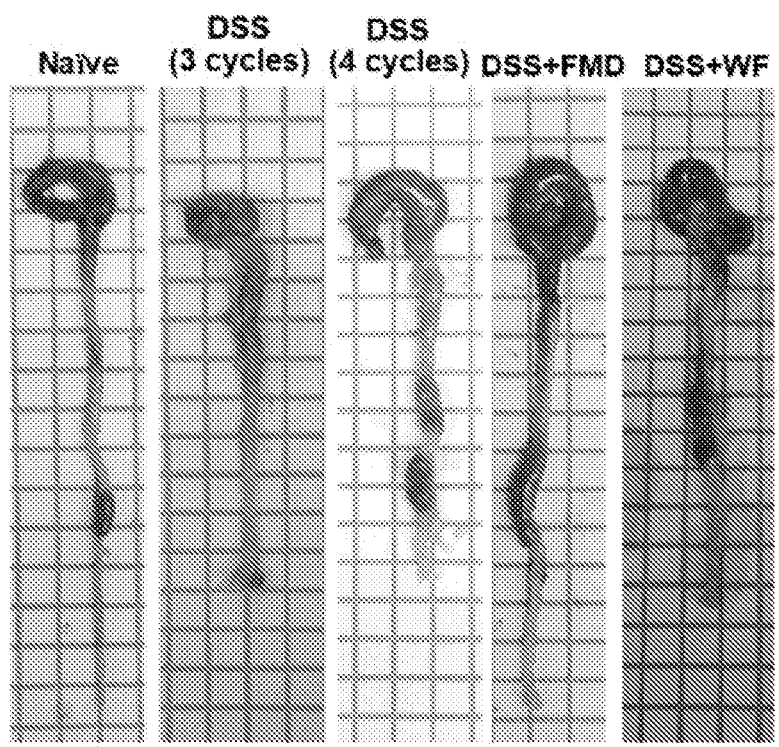
FIG. 4A provides a visual representation of murine colon length from Naïve, DSS control diet after 3 cycles (DSS 3 cycles), DSS control diet after four cycles (DSS 4 cycles), DSS control diet after 4 cycles of DSS plus 2 cycles of FMD (DSS+FMD) and DSS control diet plus 2 cycles of water-only fasting (DSS+WF) groups.
Figure 4B:
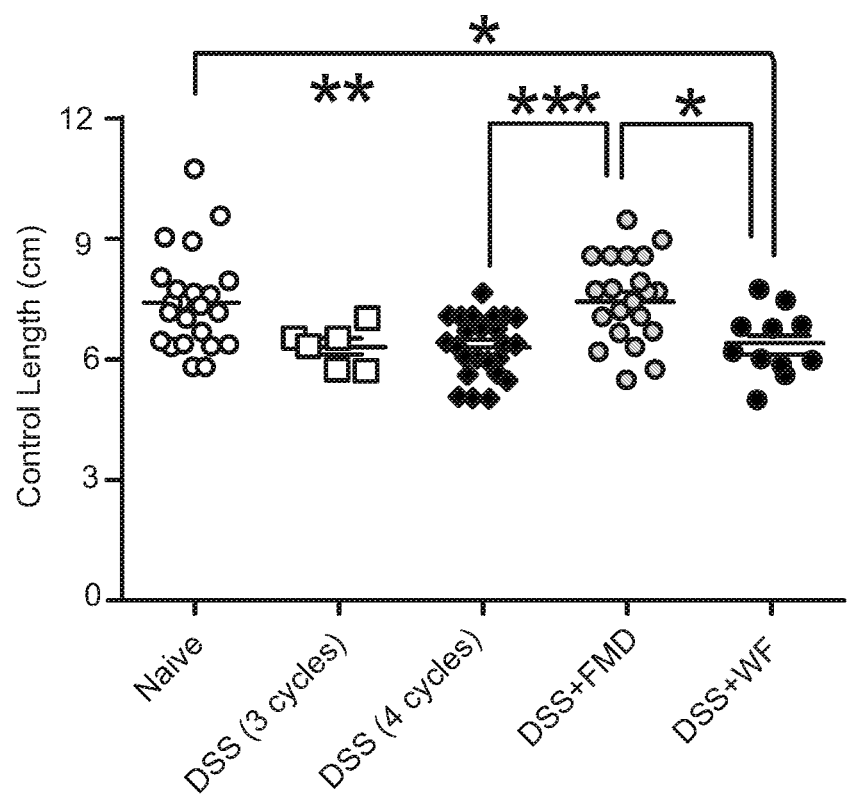
FIG. 4B provides quantification of colon lengths of the Naïve, DSS control diet after 3 cycles, DSS control diet, DSS control diet plus 2 cycles of FMD, and DSS control diet plus 2 cycles of water-only fasting. (One-way ANOVA, *p<0.05, p<0.01, *p<0.001).

FIGS. 4A-B shows that regeneration of colon is enhanced in the DSS+FMD group compared to the DSS+WF group after 4 cycles of DSS. FIG. 4A provides a visual representation of murine colon length from Naïve, DSS control diet after 3 cycles (DSS 3 cycles), DSS control diet after four cycles (DSS 4 cycles), DSS control diet after 4 cycles of DSS plus 2 cycles of FMD (DSS+FMD) and DSS control diet plus 2 cycles of water-only fasting (DSS+WF) groups. FIG. 4B provides quantification of colon lengths of the Naïve, DSS control diet after 3 cycles, DSS control diet, DSS control diet plus 2 cycles of FMD, and DSS control diet plus 2 cycles of water-only fasting. (One-way ANOVA, *p<0.05, p<0.01, *p<0.001).

Figure 5A:
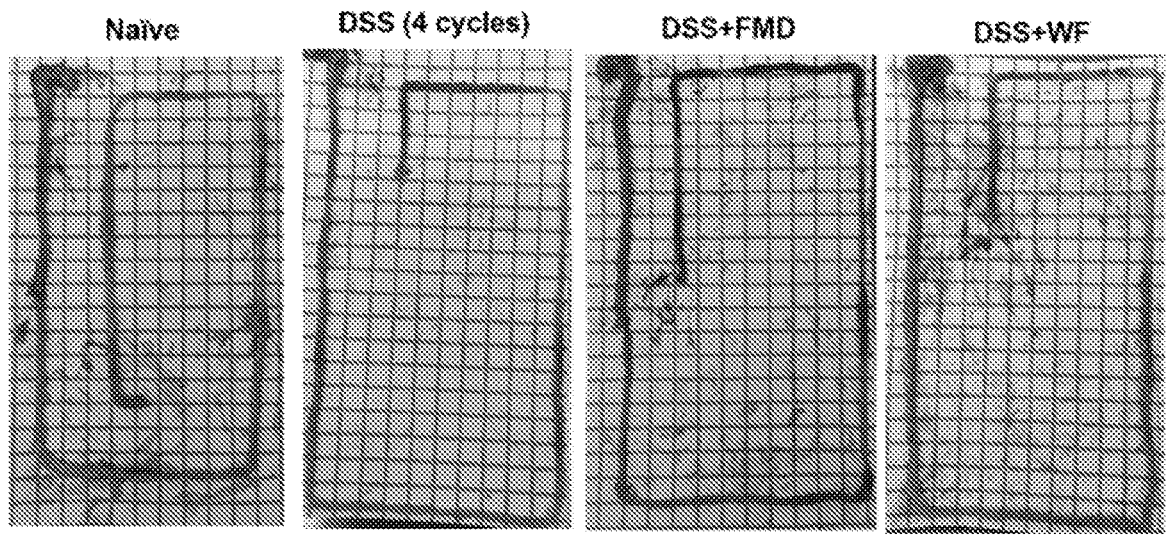
FIG. 5A provides a visual representation of murine small intestine from Naïve, DSS control diet after 3 cycles (DSS 3 cycles), DSS control diet after four cycles (DSS 4 cycles), DSS control diet after 4 cycles of DSS plus 2 cycles of FMD (DSS+FMD) and DSS control diet plus 2 cycles of water-only fasting (DSS+WF) groups.
Figure 5B:
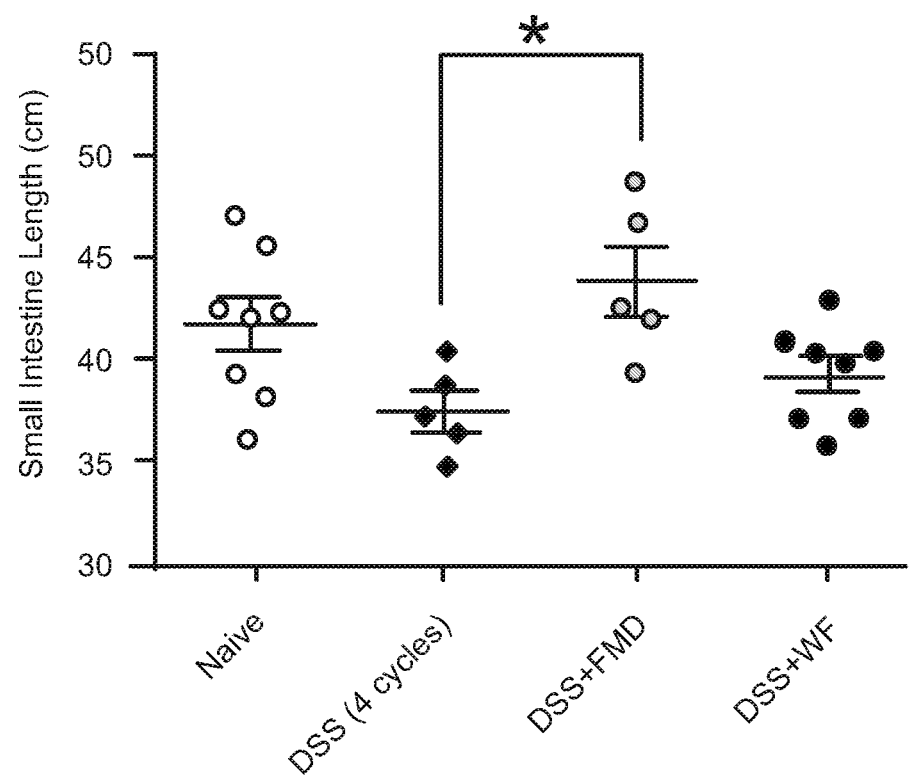
FIG. 5B provides quantification of small intestine lengths of the Naïve, DSS control diet (DSS), DSS control diet plus 2 cycles of FMD (DSS+FMD), and DSS control diet plus 2 cycles of water-only fasting (DSS+WF). (One-way ANOVA, *p<0.05).

FIGS. 5A and 5B provide experimental results showing regeneration of small intestine is enhanced in the DSS+FMD group with no change in the DSS+WF group after 4 cycles of DSS. FIG. 5A provides a visual representation of murine small intestine from Naive, DSS control diet after 3 cycles (DSS 3 cycles), DSS control diet after four cycles (DSS 4 cycles), DSS control diet after 4 cycles of DSS plus 2 cycles of FMD (DSS+FMD) and DSS control diet plus 2 cycles of water-only fasting (DSS+WF) groups. FIG. 5B provides quantification of small intestine lengths of the Naïve, DSS control diet (DSS), DSS control diet plus 2 cycles of FMD (DSS+FMD), and DSS control diet plus 2 cycles of water-only fasting (DSS+WF). (One-way ANOVA, *p<0.05).

Figure 6A:
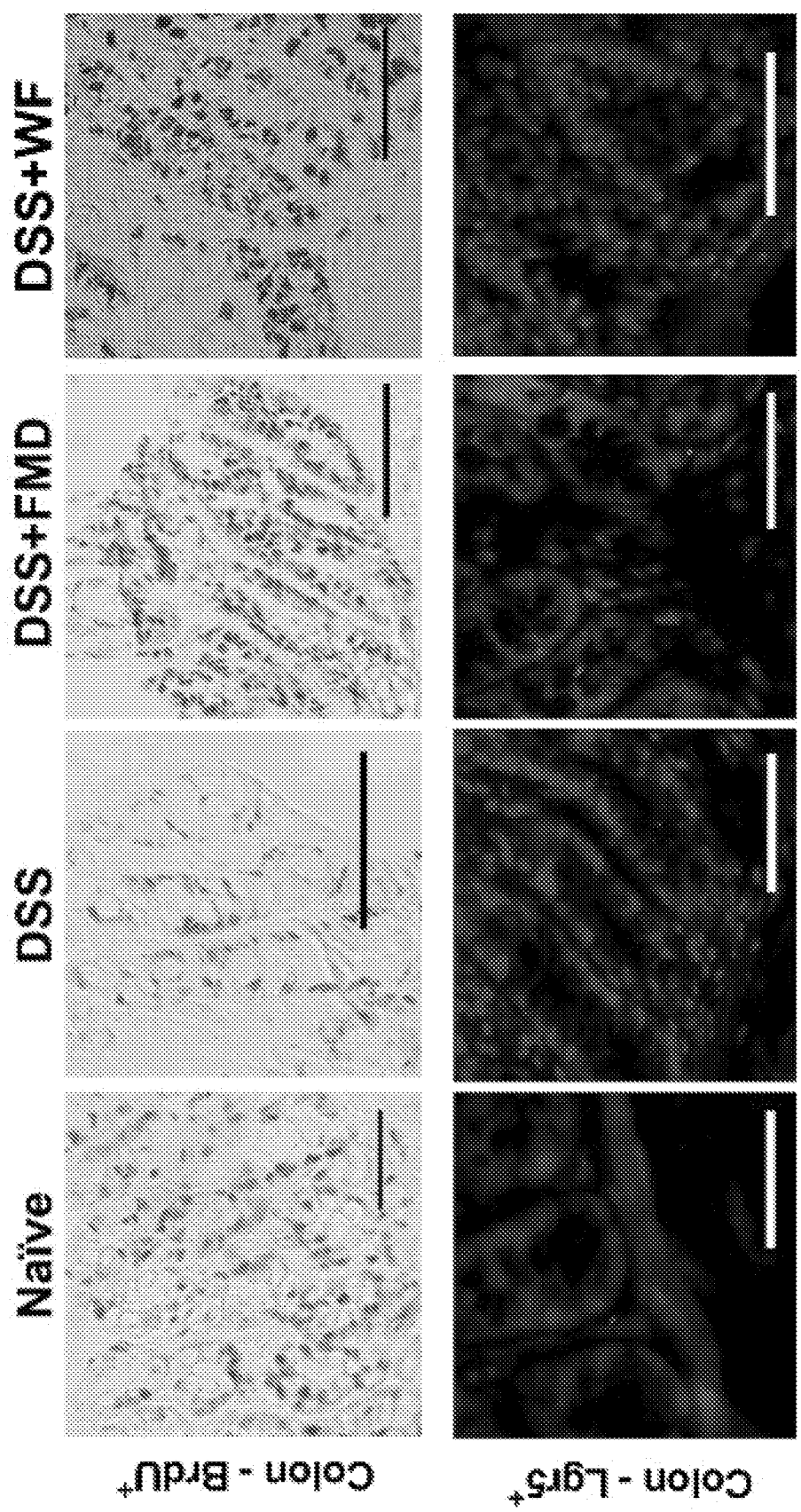
FIG. 6A provides immunohistochemistry for BrdU$^+$ cells and for Lgr5+cells in proximal colonic crypts of murine colon ICC sections in Naïve, DSS control diet (DSS), DSS control diet plus 2 cycles of FMD (DSS+FMD) groups, and DSS control diet plus 2 cycles of water-only fast (DSS+WF).
Figure 6C:
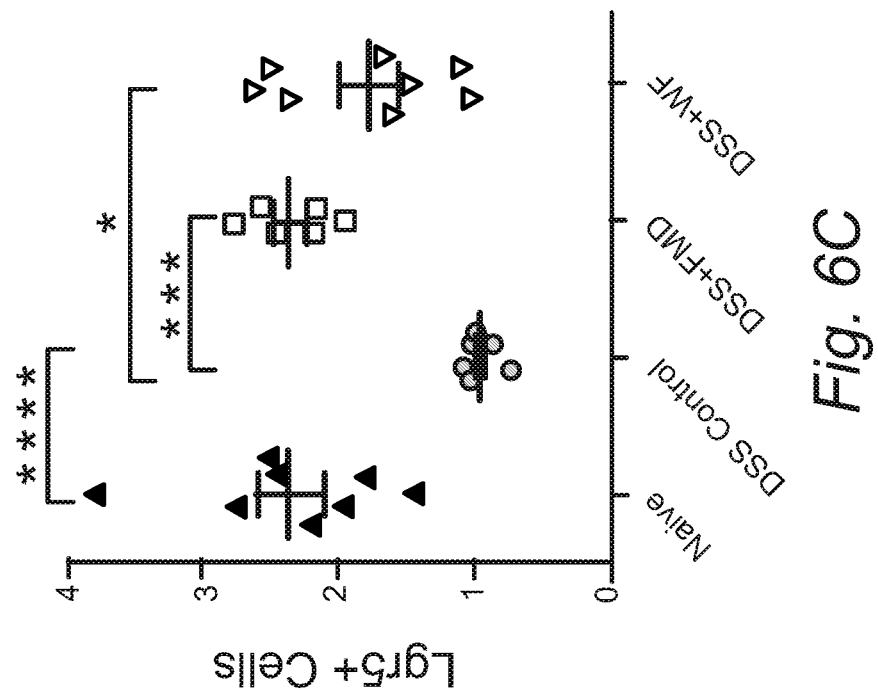
FIG. 6C provides Quantification of Lgr5$^+$ cells per proximal colonic crypt in Naïve (n=8), DSS control diet (DSS), DSS control diet plus 2 cycles of FMD (DSS+FMD), and DSS control diet plus 2 cycles of water-only fasting (DSS+WF) groups.
Figure 6B:
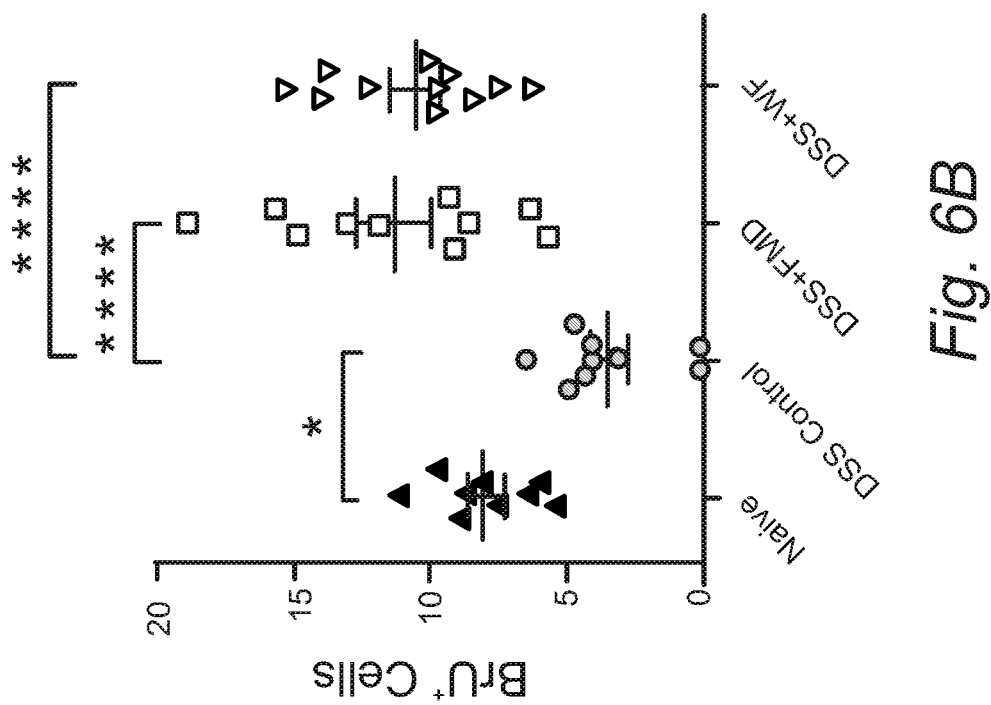
FIG. 6B provides quantification of BrdU$^+$ cells per proximal colonic crypt in Naïve, DSS control diet (DSS), DSS control diet plus 2 cycles of FMD (DSS+FMD), and DSS control diet plus 2 cycles of water-only fasting (DSS+WF) groups.

FIG. 6A provide experimental results showing that markers for regeneration in the colon (BrdU and Lgr5) are increased in the DSS+FMD and DSS+WF group, with the DSS+FMD group having a greater increase in Lgr5 in colonic crypts. FIG. 6A shows immunohistochemistry for BrdU$^+$ cells and for Lgr5+cells in proximal colonic crypts of murine colon ICC sections in Naïve, DSS control diet (DSS), DSS control diet plus 2 cycles of FMD (DSS+FMD) groups, and DSS control diet plus 2 cycles of water-only fast (DSS+WF). FIG. 6B provides quantification of BrdU$^+$ cells per proximal colonic crypt in Naïve, DSS control diet (DSS), DSS control diet plus 2 cycles of FMD (DSS+FMD), and DSS control diet plus 2 cycles of water-only fasting (DSS+WF) groups. FIG. 6C provides quantification of Lgr5$^+$ cells per proximal colonic crypt in Naïve (n=8), DSS control diet (DSS), DSS control diet plus 2 cycles of FMD (DSS+FMD), and DSS control diet plus 2 cycles of water-only fasting (DSS+WF) groups. (one-way ANOVA, *p <0.05, p <0.01, *p <0.001, and ****p<0.0001).

Figure 7A:
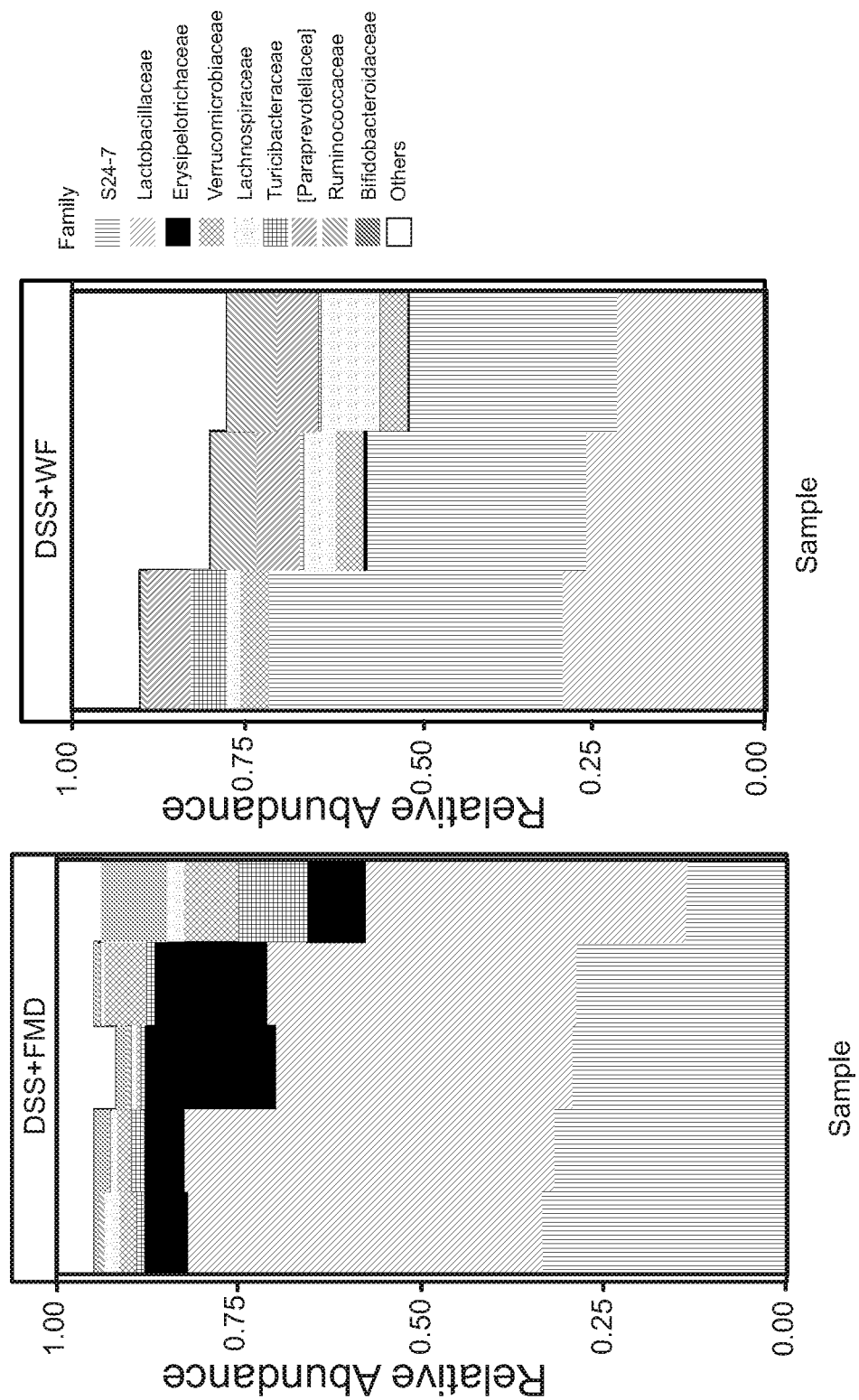
FIG. 7A provides a plot showing microbiota shifts in the DSS+FMD group 9 days after the 4th DSS cycle/two days after the 2nd FMD cycle, and the DSS+WF group 9 days after the $4^{th}$ DSS cycle/four days after the $2^{nd}$ water-only fast.

FIG. 7A provides a plot showing microbiota shifts in the DSS+FMD group 9 days after the 4th DSS cycle/two days after the 2nd FMD cycle, and the DSS+WF group 9 days after the 4$^{th}$ DSS cycle/four days after the 2$^{nd}$ water-only fast. FIG. 7B provides a table summarizing the top 8 most abundant families in fecal samples between the groups at these timepoints. *Lactobacilaceae* is reduced in the DSS+WF group compared to the DSS+FMD group (25.8+3.97% vs. 45.2+4.2%), as well as in *Erysipelotrichaceae* (0.286+0.184% vs. 10.5+5.71%), with no detectable presence of *Bifidobacteriaceae*. *Paraprevotellaceae* is present in the DSS+WF group but not in the DSS+FMD group (6.13+0.148%).

Figure 8A:
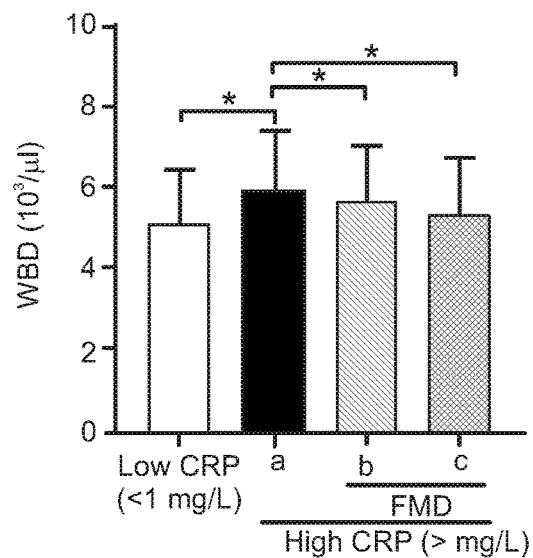
FIG. 8A provides a plot of WBC count ($10^3/\mu l$) from patients with low CRP (<1 mg/L; n=36) or high CRP (>1 mg/L) prior to dietary intervention (a), at the end of an initial 5-day FMD cycle before resuming normal food intake (b), and approximately 5 days after completing 3 FMD cycles and refeeding (c).
Figure 8B:
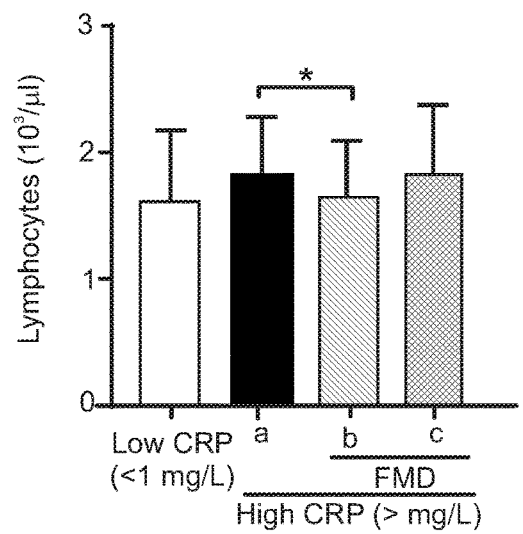
FIG. 8B provides a plot of circulating lymphocyte count ($10^3/\mu l$) from patients with low CRP (<1 mg/L; n=36) or high CRP (>1 mg/L) prior to dietary intervention (a), at the end of an initial 5-day FMD cycle before resuming normal food intake (b), and approximately 5 days after completing 3 FMD cycles and refeeding (c).
Figure 8C:
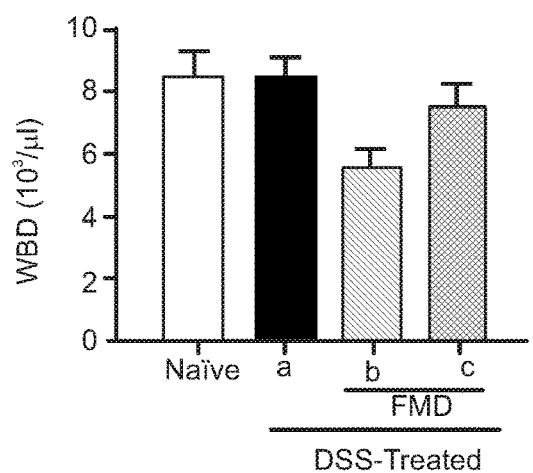
FIG. 8C provides a plot of WBC counts ($10^3/\mu l$) in untreated, naive mice or mice that received 4 cycles of DSS (a), on the last day of 1 cycle of a 4-day FMD between the $3^{rd}$ and last DSS cycles (b), and two days after 4 DSS cycles and 2 FMD cycles (c).
Figure 8D:
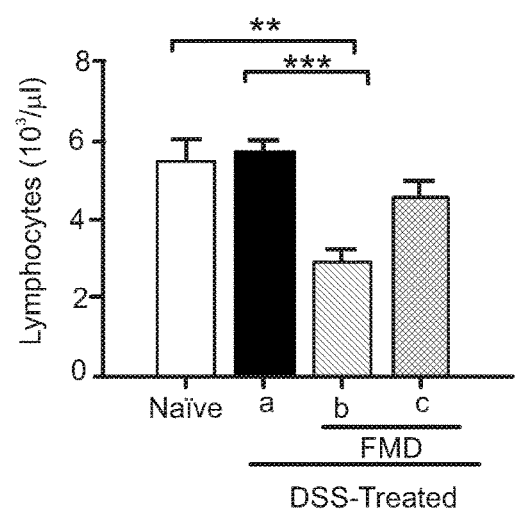
FIG. 8D provides a plot of Circulating lymphocyte counts ($10^3/\mu l$) in untreated, Naïve mice or mice that received 4 cycles of DSS (a), on the last day of 1 cycle of a 4-day FMD between the $3^{rd}$ and last DSS cycles (b), and two days after 4 DSS cycles and 2 FMD cycles (c). Data are presented as mean±SEM.

FIG. 8A-D provide plots showing that white blood cell (WBC) and lymphocyte counts in humans and mice with systemic inflammation improves after treatment with FMD cycles. FIG. 8A provides a plot of WBC count ($10^3/\mu l$) from patients with low CRP (<1 mg/L; n=36) or high CRP (>1 mg/L) prior to dietary intervention (a), at the end of an initial 5-day FMD cycle before resuming normal food intake (b), and approximately 5 days after completing 3 FMD cycles and refeeding (c). FIG. 8A provides a plot of circulating lymphocyte count ($10^3/\mu l$) from patients with low CRP (<1 mg/L; n=36) or high CRP (>1 mg/L) prior to dietary intervention (a), at the end of an initial 5-day FMD cycle before resuming normal food intake (b), and approximately 5 days after completing 3 FMD cycles and refeeding (c). FIG. 8C provides a plot of WBC counts ($10^3/\mu l$) in untreated, naïve mice or mice that received 4 cycles of DSS (a), on the last day of 1 cycle of a 4-day FMD between the 3$^{rd}$ and last DSS cycles (b), and two days after 4 DSS cycles and 2 FMD cycles (c). FIG. 8D provides a plot of Circulating lymphocyte counts ($10^3/\mu l$) in untreated, naïve mice or mice that received 4 cycles of DSS (a), on the last day of 1 cycle of a 4-day FMD between the 3$^{rd}$ and last DSS cycles (b), and two days after 4 DSS cycles and 2 FMD cycles (c). Data are presented as mean±SEM. (one-way ANOVA, *p <0.05, p <0.01, and *p <0.001).

Details of an Exemplary Prolon™ Fasting Mimicking Diet

In an embodiment of the present invention, a diet package for administering a fasting mimicking diet is provides. The fasting mimicking diet package provides daily meal portions for a predetermined number of days. Typically, the predetermined number of days is from 1 to 10 days (i.e., 1, 2, 3, 4, 5, 6, 7, 8, 9, or 10 days). In a particularly useful variation, the predetermined number of days is 5 or 6 days. In some variations, the fasting mimicking diets set forth herein provide a subject at most, in increasing order of preference, 75%, 50%, 40%, 30%, or 10% of the subject's normal caloric intake or the daily recommended caloric intake for a subject. In a refinement, the fasting mimicking diet provides at least, in increasing order of preference, 5%, 10%, or 20% of the subject's normal caloric intake or the daily recommended caloric intake for a subject. However, if the fasting mimicking diet composition is maintained, based on our current and previous findings, partial disease prevention and treatment effects are anticipated even if 100% of the normal caloric intake is provided to subjects. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the fasting mimicking diet provides the subject with 700 to 1200 kcal/day. In a particularly useful refinement, the fasting mimicking diet provides a male subject of average weight with about 1100 kcal/day and a female subject of average weight with 900 kcal/day. In some variation, the diet from the diet package is administered on consecutive days. In another variation, the daily meal portions provided for only one day a week for at least a month.

In one embodiment, the fasting mimicking diet package providing daily meal portions for a predetermined number of days as set forth above. The fasting mimicking diet package includes a kale cracker composition, a first vegetable broth composition, a mushroom soup composition, a tomato soup composition, a quinoa-containing minestrone soup composition, a bean-containing minestrone soup composition, and a pumpkin soup composition. Characteristically, the daily meal portions are packaged into meal servings or into a total daily serving to be divided into meals. In a refinement, the fasting mimicking diet package further includes a nut-containing nutrition bar, a cocoa-containing nutrition bar, a first olive-containing composition, a first vegetable broth composition, a tea composition that includes spearmint, a energy drink composition, a micro-nutritional composition, and a algal oil composition. In a further refinement, the fasting mimicking diet package further includes a second olive-containing composition, a second vegetable broth composition, a tea composition that includes spearmint and lemon, and a tea composition that includes hibiscus.

In a variation of the embodiments set forth above, the fasting mimicking diet package includes daily meal portions that provide less than 40 grams of sugar for day 1, less than 30 grams of sugar for days 2 to 5 and any remaining days, less than 28 grams of protein for day 1, less than 18 grams of protein for days 2 to 5 and any remaining days, 20-30 grams of monounsaturated fats or more to reach the desired caloric intake (i.e., a predetermined caloric intake) for day 1, 6-10 grams of polyunsaturated fats or more to reach the desired caloric intake for day 1, 2-12 grams of saturated fats or more to reach the desired caloric intake for day 1, 10-15 grams of monounsaturated fats or more to reach the desired caloric intake for days 2 to 5 and any remaining days, 3-5 grams of polyunsaturated fats or more to reach the desired caloric intake for days 2 to 5 and any remaining days, 1-6 grams of saturated fats or more to reach the desired caloric intake for days 2 to 5, or any remaining days, and a micronutrient composition on each day and any remaining days.

In another variation of the embodiments set forth above, the fasting mimicking diet package includes daily meal portions 8-10 kcal per kilogram body weight for each diet day. In this variation, the fasting mimicking diet provides less than 30 grams of sugar for each diet day, less than 18 grams of protein for each diet day, 9-15 grams of monounsaturated fats or more to reach the desired caloric intake for each diet day, and 2.5-4.5 grams of polyunsaturated fats or more to reach the desired caloric intake for each diet day and 1-5.5 grams of saturated fats or more to reach the desired caloric intake for each diet day. Higher levels of the fats listed above can be provided for higher FMD formulation providing up to 100% of the normal caloric intake to subjects.

In still another variation of the embodiments set forth above, the fasting mimicking diet package includes daily meal portions that provide 5-8 kcal per kilogram body weight for each diet day. In this variation, the fasting mimicking diet provides less than 20 grams of sugar for each diet day, less than 12 grams of protein for each diet day, and 6.5-10 grams of monounsaturated fats or more to reach the desired caloric intake for each diet day, 2.5-4.5 grams of polyunsaturated fats or more to reach the desired caloric intake for each diet day and 1.5-4 grams of saturated fats or more to reach the desired caloric intake for each diet day.

In still another variation of the embodiments set forth above, the fasting mimicking diet package includes daily meal servings that provide 0-3 kcal per kilogram body weight for each diet day. In this variation, the fasting mimicking diet provides less than 5 grams of sugar for each diet day, less than 3 grams of protein for each diet day, and less than 2.5 grams of monounsaturated fats for each diet day, less than 1 grams of polyunsaturated fats for each diet day and less than 1 grams of saturated fats for each diet day.

In an embodiment, the nutritional requirements for the fasting mimicking diet set forth above can be realized by a diet package with certain specific meal components. In one variation, the fasting mimicking diet package provides daily meal portions for a predetermined number of days are set forth above (e.g., 1, 2, 3, 4, 5, 6, 7, 8, 9, or 10 days). The fasting mimicking diet package includes a kale cracker composition , a first vegetable broth composition, a mushroom soup composition, a tomato soup composition, a quinoa-containing minestrone soup composition, a bean-containing minestrone soup composition, and a pumpkin soup composition, Characteristically, the daily meal portions are packaged into meal servings or into a total daily serving to be divided into meals. In a refinement, the fasting mimicking diet package further includes a nut-containing nutrition bar, a cocoa-containing nutrition bar, a first olive-containing composition, a first vegetable broth composition, a tea composition that includes spearmint, a energy drink composition, a micronutritional composition, and a algal oil composition. In a further refinement, the fasting mimicking diet package further includes a second olive-containing composition, a second vegetable broth composition, a tea composition that includes spearmint and lemon, and a tea composition that includes hibiscus. It should be appreciated that each of the soup, broth, tea and energy compositions set forth herein are designed to have added water when consumed.

In another variation of a fasting mimicking diet package, diet package includes a nut-containing nutrition bar, a cocoa-containing nutrition bar, a first olive-containing composition, a kale cracker composition, a vegetable soup composition, a first vegetable broth composition, a tea composition that includes spearmint, a energy drink composition, a micronutritional composition, and a algal oil composition. Characteristically, the daily meal portions are packaged into meal servings or into a total daily serving to be divided into meals. This diet package also includes daily meal portions for a predetermined number of days as set forth above with the daily meal portions being packaged into meal servings or into a total daily serving to be divided into meals. In a refinement, the fasting mimicking diet package further includes a mushroom soup composition, a tomato soup composition, a quinoa-containing minestrone soup composition, and a pumpkin soup composition. In a further refinement, the fasting mimicking diet package further includes a second olive-containing composition, a second vegetable broth composition, a bean-containing minestrone soup composition, a tea composition that includes spearmint and lemon, and a tea composition that includes hibiscus.

As set forth above, the fasting mimicking diet packages includes specific meal components. Typically, compositions are as follows. The nut-containing nutrition bar includes almond meal and macadamia nuts. The cocoa-containing nutrition bar includes almond butter, almonds, and brown rice crispy (e.g., brown puffed rice). The mushroom soup composition includes brown rice powder, carrots, inulin, and mushrooms. The bean-containing minestrone soup composition includes white beans, cabbage, and potatoes. The first vegetable broth composition includes carrots, maltodextrin, celery, spinach, and tomatoes. The second vegetable broth composition includes carrots, maltodextrin, celery, spinach, soy lecithin, and tomatoes. The energy drink composition includes glycerin and water. The algal oil composition includes schizocatrium algae oil. The micronutrient composition includes beet root powder, calcium carbonate, carrots, collard leaf, kale leaf, and tomatoes. In a refinement, the micronutrient composition includes Vit A, Vit C, Ca, Fe, Vit D3, Vit E, Vit K, Vit B1, Vit B2, Vit B3, Vit B5, Vit B6, Vit B7, Vit B9, Vit B12, Cr, Cu, I, Mg, Mn, Mo, Se, and Zn.

In a refinement, the nut-containing nutrition bar (L-Bar Nut based) includes almond meal and macadamia nuts. In a refinement, the nut-containing nutrition bar (L-Bar Nut based) includes almond meal preferably in an amount of 20 to 35 weight %; coconut preferably in an amount of 2 to 10 weight %; coconut oil preferably in an amount of 1 to 8 weight %; flax seed meal preferably in an amount of 1 to 8 weight %; honey preferably in an amount of 10 to 30 weight %; macadamia nuts preferably in an amount of 10 to 30 weight %; pecans preferably in an amount of 10 to 25 weight %; salt preferably in an amount of 0.1 to 0.8 weight %; and optionally vanilla preferably in an amount of 0.3 to 1.5 weight %.

In a refinement, the cocoa-containing nutrition bar (L-Bar ChocoCrisp) includes almond butter, almonds, and brown rice crispy (PGP10235). In a refinement, the cocoa-containing nutrition bar (L-Bar ChocoCrisp) includes almond butter preferably in an amount of 10 to 25 weight %; almonds preferably in an amount of 3 to 12 weight %; brown rice crispy (PGP10235) preferably in an amount of 10 to 25 weight %; brown rice syrup preferably in an amount of 2 to 8 weight %; chocolate liquor preferably in an amount of 1 to 4 weight %, cocoa butter preferably in an amount of 0.4 to 1.6 weight %; cocoa powder preferably in an amount of 4 to 12 weight %; fiber syrup SF75 preferably in an amount of 18 to 38 weight %, flax seed oil preferably in an amount of 1 to 3 weight %; salt preferably in an amount of 0.1 to 0.4 weight % and sugar preferably in an amount of 1 to 6 weight %.

In a refinement, the first olive-containing composition (sea salt version) incudes olives, olive oil, and sea salt. In a refinement, the first olive-containing composition (sea salt) includes lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; and thyme preferably in an amount of 0.1 to 0.5 weight %.

In a refinement, the second olive-containing composition (garlic version) incudes olives, olive oil, and garlic. In a refinement, the second olive-containing composition (garlic) includes garlic preferably in an amount of 0.1 to 0.6 weight %; lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; thyme preferably in an amount of 0.1 to 0.5 weight %.

In a refinement, the kale cracker composition includes kale, almonds, tapioca flour, and optionally sesame seeds. In another refinement, the kale cracker composition includes almonds preferably in an amount of 15 to 40 weight %; black pepper preferably in an amount of 0.1 to 0.4 weight %; chia seeds preferably in an amount of 3 to 10 weight %; chili pepper preferably in an amount of 0.4 to 1.2 weight %; cumin seeds preferably in an amount of 0.3 to 0.9 weight %; flax seeds preferably in an amount of 3 to 10 weight %; garlic preferably in an amount of 0.02 to 0.04 weight %; kale preferably in an amount of 2 to 6 weight %; oil (sun flower) preferably in an about of 2 to 7 weight %; onion (powder, minced) typically in an amount of 0.3 to 0.9 weight %; oregano preferably in an amount of 0.01 to 0.06 weight %; salt preferably in an amount of 1 to 4 weight %; sesame seeds preferably in an amount of 15 to 35 weight %; sugar (coconut) preferably in an amount of 1 to 5 weight %; tapioca flour preferably in an amount of 10 to 30 weight %; vinegar (coconut) preferably in an amount of 1 to 4 weight %; water (purified) preferably in an amount of 2 to 12 weight %; and yeast extract preferably in an amount of 0.3 to 1 weight %.

In another refinement, the kale cracker composition includes kale, flax seeds golden, sesame seeds, and sunflower seeds. In another refinement, the apple cider vinegar preferably in an amount 1 to 3 weight %; black pepper preferably in an amount of 0.4 to 1.3 weight %; cashews preferably in an amount of 4 to 13 weight %; dill weed preferably in an amount of 0.4 to 1.3 weight %; flax seeds golden preferably in an amount of 13 to 40 weight %; hemp seeds preferably in an amount of 0.7 to 2 weight %; kale preferably in an amount of 14 to 42 weight %; onion, white, dried, (powder, minced) preferably in an amount of 0.5 to 1.6 weight %; pumpkin seeds preferably in an amount of 0.7 to 2 weight %; salt (reg. , kosher, sea salt) preferably in an amount of 0.7 to 2 weight %; Sesame seeds preferably in an amount of 2 to 8 weight %; sunflower seeds preferably in an amount of 10 to 30 weight %; and yeast extract preferably in an amount of 1 to 5 weight %.

In a refinement, the vegetable soup composition includes onions, tomatoes, spinach, green tree extract, optionally rice flour, optionally brown rice powder, optionally carrots, and optionally inulin, leeks, In a refinement, the vegetable soup composition includes basil (whole leaf, dried) preferably in an amount of 0.3 to 0.9 weight %; brown rice powder (whole grain) preferably in an amount of 3 to 12 weight %; carrot (dehydrated, puffed, powder, pieces) preferably in an amount of 4 to 14 weight %; green tea extract preferably in an amount of 0.02 to 0.06 weight %; inulin preferably in an amount of 5 to 15 weight %; leeks (granules −10+40)

preferably in an amount of 1 to 5 weight %; oil (olive) preferably in an amount of 1 to 6 weight %; onion (powder, minced) preferably in an amount of 4 to 15 weight %; parsley preferably in an amount of 0.3 to 0.8 weight %; red bell peppers preferably in an amount of 1 to 5 weight %; rice flour preferably in an amount of 18 to 50 weight %; salt preferably in an amount of 2 to 7 weight %; spinach (leaf, powder) preferably in an amount of 0.4 to 1.5 weight %; tomatoes (fruit powder, sun dried, granules) preferably in an amount of 4 to 14 weight %; yeast extract preferably in an amount of 0.5 to 1.8 weight %. In the vegetable soup composition and any of the compositions set forth herein having rice flour, the rice flour can be glutinous or non-glutinous, milled or unmilled.

In another refinement, the vegetable soup composition includes carrots, inulin, leeks, onions and rice flour. In a refinement, the vegetable soup composition includes basil, whole leaf, dried preferably in an amount of 0.3 to 1 weight %; carrot (dehydrated, puffed, powder, pieces) preferably in an amount of 4 to 12 weight %; inulin preferably in an amount of 6 to 18 weight %; leeks in an amount of 1 to 5 weight %; oil (olive) preferably in an amount of 1 to 3 weight %; Onion, white, dried, (powder, minced) preferably in an amount of 10 to 30 weight %; parsley preferably in an amount of 0.3 to 1 weight %; potato preferably in an amount of 1 to 5 weight %; red pepper preferably in an amount of 1 to 6 weight %; rice flour in an amount of 13 to 40 weight %; salt (reg., kosher, sea salt) in an amount of 4 to 12 weight %; spinach (leaf, powder) preferably in an amount of 0.2 to 1 weight %; and tomatoes, (fruit powder, sun dried granules) preferably in an amount of 3 to 13 weight %.

In a refinement, the mushroom soup composition includes mushrooms, green tea extract, optionally brown rice powder, optionally carrots, and optionally inulin. In a refinement, the mushroom soup composition includes brown rice powder (whole grain) preferably in an amount of 10 to 30 weight %; carrot (dehydrated, puffed, powder, pieces) preferably in an amount of 3 to 12 weight %; green tea extract preferably in an amount of 0.02 to 0.06 weight %; inulin preferably in an amount of 3 to 12 weight %; mushrooms (European mix, powder, pieces) preferably in an amount of 6 to 18 weight %; oil (olive) preferably in an amount of 1 to 6 weight %; onion preferably in an amount of powder, minced) preferably in an amount of 3 to 12 weight %; parsley preferably in an amount of 0.1 to 0.5 weight %; rice flour preferably in an amount of 18 to 50 weight %; salt preferably in an amount of 2 to 8 weight %; yeast extract preferably in an amount of 0.5 to 1.5 weight %.

In another refinement, the mushroom soup composition includes carrots, inulin, mushrooms, onions, and rice flour. In another refinement, the mushroom soup composition includes carrot (dehydrated, puffed, powder, pieces) preferably in an amount of 7 to 22 weight %; inulin preferably in an amount of 7 to 22 weight %; mushrooms (European mix), (powder & pieces) dehydrated preferably in an amount of 7 to 22 weight %; oil (olive) preferably in an amount of 0.6 to 2 weight %; Onion, white, dried, (powder, minced) preferably in an amount of 7 to 22 weight %; parsley preferably in an amount of 0.3 to 0.9 weight %; potato preferably in an amount of 0.6 to 2 weight %; rice flour preferably in an amount of 15 to 45 weight %; salt (reg., kosher, sea salt) preferably in an amount of 6 to 18 weight %; and yeast extract preferably in an amount of 0.7 to 2.2 weight %.

In a refinement, the tomato soup composition includes tomatoes, green tea extract, optionally inulin, and optionally onions. In a refinement, the tomato soup composition (new) includes basil (whole leaf, dried) preferably in an amount of 0.2 to 0.7 weight %; brown rice powder (whole grain) preferably in an amount of 1 to 5 weight %; green tea extract preferably in an amount of 0.02 to 0.06 weight %; inulin preferably in an amount of 7 to 20 weight %; oil (olive) preferably in an amount of 3 to 9 weight %; onion preferably (powder, minced) preferably in an amount of 4 to 12 weight %; parsley preferably in an amount of 0.1 to 0.6 weight %; rice flour preferably in an amount of 18 to 50 weight %; salt preferably in an amount of 2 to 9 weight %; tomatoes (fruit powder, sun dried, granules) preferably in an amount of 12 to 36 weight %; and yeast extract preferably in an amount of 0.5 to 3 weight %.

In another refinement, the tomato soup composition includes tomatoes, inulin, olives, onions, potatoes, and rice flour. In still another refinement, the tomato soup composition includes basil, whole leaf, dried preferably in an amount of 0.3 to 1 weight %; inulin preferably in an amount of 6 to 18 weight %; oil (olive) preferably in an amount of 4 to 14 weight %; onion, white, dried, (powder, minced) preferably in an amount of 8 to 24 weight %; parsley preferably in an amount of 0.3 to 0.9 weight %; potato preferably in an amount of 6 to 18 weight %; rice flour preferably in an amount of 9 to 27 weight %; salt (reg., kosher, sea salt) preferably in an amount of 4 to 14 weight %; tomatoes, (fruit powder, sun dried granules) preferably in an amount of 8 to 24 weight %; and yeast extract preferably in an amount of 0.7 to 2.2 weight %.

In a refinement, the quinoa-containing minestrone soup composition includes quinoa, green tea extract, optionally olive oil, optionally cabbage, optionally potatoes, optionally rice flour, and optionally tomatoes and optionally no tumeric. In a refinement, the quinoa-containing minestrone soup composition includes basil (whole leaf, dried preferably in an amount of 0.7 to 2 weight %; broccoli powder preferably in an amount of 0.6 to 2 weight %; cabbage white (flakes) preferably in an amount of 3 to 10 weight %; carrot (dehydrated, puffed, powder, pieces) preferably in an amount of 3 to 10 weight %; celery preferably in an amount of 1 to 4 weight %; celery seeds (powder) preferably in an amount of 0.07 to 0.2 weight %; garlic preferably in an amount of 0.7 to 2 weight %; green tea extract preferably in an amount of 0.02 to 0.06 weight %; inulin preferably in an amount of 1 to 5 weight % ; leeks (granules −10+40), preferably in an amount of 0.7 to 2 weight %; oil (olive) preferably in an amount of 0.6 to 2 weight %; onion (powder, minced) preferably in an amount of 2 to 8 weight %; peas preferably in an amount of 3 to 10 weight %; potato preferably in an amount of 7 to 20 weight %; quinoa preferably in an amount of 7 to 20 weight %; rice flour preferably in an amount of 7 to 20 weight %; salt, preferably in an amount of 1 to 6 weight %; spinach (leaf, powder) preferably in an amount of 0.5 to 2 weight %; tomatoes (fruit powder, sun dried, granules) preferably in an amount of 2 to 6 weight %; yeast extract preferably in an amount of 0.6 to 2 weight %; zucchini (powder, diced) preferably in an amount of 2 to 8 weight %.

In another refinement, the quinoa-containing minestrone soup includes quinoa, cabbage, potatoes, and rice flour. In still another refinement, the quinoa-containing minestrone soup includes basil, whole leaf, dried preferably in an amount of 0.7 to 2.2 weight %; broccoli powder preferably in an amount of 0.7 to 2.2 weight %; cabbage white (flakes) preferably in an amount of 0.6 to 2.2 weight %; carrot (dehydrated, puffed, powder, pieces) preferably in an amount of 3 to 10 weight %; celeriac preferably in an amount of 2 to 6 weight %; celery seeds powder preferably in an amount of 0.6 to 1.8 weight %; garlic preferably in an amount of 1 to 3 weight %; Onion, white, dried, (powder, minced) preferably in an amount of 3 to 9 weight %; peas preferably in an amount of 3 to 10 weight %; potato preferably in an amount of 6 to 20 weight %; quinoa preferably in an amount of 8 to 23 weight %; rice flour preferably in an amount of 7 to 22 weight %; salt (reg., kosher, sea salt) preferably in an amount of 2 to 7 weight %; savoy cabbage preferably in an amount of 3 to 10 weight %; spinach (leaf, powder) preferably in an amount of 0.7 to 2.2 weight %; turmeric preferably in an amount of 0.6 to 1.8 weight %; yeast extract preferably in an amount of 3 to 10 weight %; and zucchini (powder, diced) preferably in an amount of 1 to 5 weight %.

In a refinement, the bean-containing minestrone soup composition includes white beans (e.g., great northern beans), great tea extract, optionally cabbage, and optionally potatoes. In a refinement, the bean-containing minestrone soup composition includes beans (great northern) preferably in an amount of 3 to 10 weight %; cabbage white (flakes) preferably in an amount of 2 to 8 weight %; carrot (dehydrated, puffed, powder, pieces) preferably in an amount of 2 to 8 weight %; celery preferably in an amount of 1 to 4 weight %; green tea extract preferably in an amount of 0.02 to 0.06 weight %; inulin preferably in an amount of 2 to 10 weight %; leeks (granules −10+40) preferably in an amount of 2 to 7 weight %; oil (olive) preferably in an amount of 2 to 7 weight %; onion (powder, minced) preferably in an amount of 2 to 7 weight %; parsley preferably in an amount of 0.2 to 1 weight %; peas preferably in an amount of 3 to 9 weight %; potato preferably in an amount of 15 to 45 weight %; rice flour preferably in an amount of 6 to 18 weight %; salt preferably in an amount of 2 to 8 weight %; spinach (leaf, powder) preferably in an amount of 0.5 to 1.5 weight %; tomatoes (fruit powder, sun dried, granules) preferably in an amount of 2 to 7 weight %; and yeast extract preferably in an amount of 0.5 to 1.5 weight %.

In a refinement, the bean-containing minestrone soup composition includes brown beans, carrots, peas, potato, and rice flour. In another refinement, the bean-containing minestrone soup composition includes carrot (dehydrated, puffed, powder, pieces) preferably in an amount of 4 to 14 weight %; celeriac preferably in an amount of 1 to 5 weight %; celery preferably in an amount of 0.5 to 1.6 weight %; leeks preferably in an amount of 2 to 8 weight %; oil (olive) preferably in an amount of 2 to 8 weight %; Onion, white, dried, (powder, minced) preferably in an amount of 3 to 10 weight %; parsley preferably in an amount of 0.5 to 1.5 weight %; peas preferably in an amount of 5 to 18 weight %; potato preferably in an amount of 8 to 24 weight %; rice flour preferably in an amount of 5 to 18 weight %; salt (reg., kosher, sea salt) preferably in an amount of 4 to 14 weight %; spinach (leaf, powder) preferably in an amount of 0.5 to 1.5 weight %; tomatoes, (fruit powder, sun dried granules) preferably in an amount of 0.9 to 2.8 weight %; turmeric preferably in an amount of 0.3 to 1.2 weight %; and yeast extract preferably in an amount of 0.5 to 1.5 weight %.

In a refinement, the pumpkin soup composition includes pumpkin, green tree extract, optionally rice flour, optionally carrots, and optionally brown rice powder. In a refinement, the pumpkin soup composition includes (new) includes brown rice powder (whole grain) preferably in an amount of 3 to 9 weight %; carrot (dehydrated, puffed, powder, pieces) preferably in an amount of 2 to 8 weight %; green tea extract preferably in an amount of 0.02 to 0.06 weight %; inulin preferably in an amount of 2 to 10 weight %; oil (olive) preferably in an amount of 1 to 7 weight %; onion (powder, minced) preferably in an amount of 1.0 to 3 weight %; pumpkin powder preferably in an amount of 20 to 60 weight %; rice flour preferably in an amount of 15 to 45 weight %; salt preferably in an amount of 2 to 10 weight %; and yeast extract preferably in an amount of 0.3 to 1 weight %.

In a refinement, the first vegetable broth includes carrots, maltodextrin, celery, spinach, and tomatoes. In a refinement, the first vegetable broth includes carrot (dehydrated, puffed, powder, pieces) preferably in an amount of 6 to 18 weight %; celery preferably in an amount of 3 to 10 weight %; garlic preferably in an amount of 3 to 10 weight %; maltodextrin preferably in an amount of 8 to 25 weight %; oil (canola) preferably in an amount of 0.5 to 2 weight %; onion (powder, minced) preferably in an amount of 6 to 18 weight %; parsley preferably in an amount of 3 to 10 weight %; potato preferably in an amount of 1 to 3 weight %; salt preferably in an amount of 7 to 21 weight %; spinach (leaf, powder) preferably in an amount of 3 to 10 weight %; tomatoes (fruit powder, sun dried, granules) preferably in an amount of 6 to 18 weight %; and yeast extract preferably in an amount of 1 to 6 weight %.

In a refinement, the second vegetable broth (chicken flavoring) includes carrots, chicken flavoring, maltodextrin, celery, spinach, soy lecithin, and tomatoes. In a refinement, the second vegetable broth composition includes carrot (dehydrated, puffed, powder, pieces) preferably in an amount of 3 to 10 weight %; celery preferably in an amount of 3 to 12 weight %; garlic preferably in an amount of 3 to 9 weight %; maltodextrin preferably in an amount of 8 to 25 weight %; oil (canola) preferably in an amount of 0.5 to 2 weight %; onion preferably in an amount of powder, minced) preferably in an amount of 3 to 12 weight %; parsley preferably in an amount of 3 to 10 weight %; potato preferably in an amount of 1 to 6 weight %; salt preferably in an amount of 8 to 25 weight %; soy lecithin preferably in an amount of 0.5 to 3 weight %; spinach (leaf, powder) preferably in an amount of 3 to 12 weight %; tomatoes (fruit powder, sun dried, granules) preferably in an amount of 6 to 18 weight %; xanthan gum preferably in an amount of 0.5 to 4 weight %; and yeast extract preferably in an amount of 4 to 12 weight %.

In a refinement, the energy drink composition includes glycerin preferably in an amount of 20 to 60 weight %; water (purified) preferably in an amount of 40 to 80 weight %.

In a refinement, the tea composition that includes spearmint includes spearmint leaves organic preferably in an amount of 70 to 100 weight %.

In a refinement, the tea composition that includes lemon and spearmint includes lemon myrtle organic preferably in an amount of 3 to 12 weight %; lemon peel organic preferably in an amount of 10 to 25 weight %; spearmint leaves organic preferably in an amount of 50 to 95 weight %.

In a refinement, the tea composition that includes hibiscus includes hibiscus tea leaves organic preferably in an amount of 80 to 100 weight %.

In a refinement, the algal oil composition includes schizocatrium algae oil (DHA Omega-3) preferably in an amount of 80 to 100 weight %.

In a refinement, the nutrient replenishment composition (NR-1) includes beet root powder, calcium carbonate, carrots, collard leaf, kale leaf, and tomatoes. In a refinement, the nutrient replenishment composition (NR-1) includes ascorbic acid preferably in an amount of 1 to 3 weight %; beet root powder preferably in an amount of 6 to 20 weight %; beta carotene preferably in an amount of 0.05 to 0.15 weight %; calcium carbonate preferably in an amount of 6 to 20 weight %; carrot (dehydrated, puffed, powder, pieces) preferably in an amount of 6 to 20 weight %; cholecaliciferol preferably in an amount of 0.00 weight %; chromuim Picolinate preferably in an amount of 0.00 weight %; collard leaf powder preferably in an amount of 6 to 20 weight %; cupric sulfate preferably in an amount of 0.01 to 0.06 weight %; cyanocobalamin, 0.00; D1-alpha tocopherol acetate preferably in an amount of 0.3 to 1 weight %; ferrous fumarate preferably in an amount of 0.2 to 1 weight %; folic acid preferably in an amount of 0.00 weight %; kale leaf preferably in an amount of 6 to 20 weight %; magnesium stearate preferably in an amount of 1 to 6 weight %; manganese sulfate preferably in an amount of 0.04 to 0.08 weight %; niacinamide preferably in an amount of 0.3 to 1 weight %; pantothenic acid preferably in an amount of 0.1 to 0.6 weight %; phytonadione preferably in an amount of 0.00 weight %; potassium iodine preferably in an amount of 0 weight %; pyriodoxine HCl preferably in an amount of 0.03 to 0.1 weight %; riboflavin preferably in an amount of 0.02 to 0.1 weight %; sodium molybdate preferably in an amount of 0.00 weight %; sodium selenate preferably in an amount of 0.00 weight %; spinach (leaf, powder) preferably in an amount of 6 to 20 weight %; thiamine mononitrate preferably in an amount of 0.02 to 0.1 weight %; tomatoes (fruit powder, sun dried, granules) preferably in an amount of 6 to 20 weight %; tribasic calcium phosphate preferably in an amount of 0.5 to 2 weight %; and zinc oxide preferably in an amount of 0.2 to 0.8 weight %.

In a variation, the each of the components of the fasting mimicking diet package and therefore the fasting mimicking diet, is substantially gluten free (e.g., each component has less than 20 ppm gluten) or very low gluten (e.g., each component has 20-100 ppm). In other variations, each of the components are provided in a serving size from 20 to 60 g. In other variations, the nut-containing nutrition bar is provided in a serving size from 30 to 60 g; cocoa-containing nutrition bar is provided in a serving size from 15 to 40 g; the olive containing composition (sea salt version) in a serving size from 10 to 20 g; the olive containing composition (garlic version) in a serving size from 10 to 20 g; kale cracker composition is provides in a serving size from 30 to 60 g; In another variation, the kale cracker compositions are provided in a serving size from 20 to 50 g; the vegetable soup compositions are provided in a serving size from 20 to 50 g; the mushroom soup compositions are provided in a serving size from 20 to 50 g; the tomato soup compositions are provided in a serving size from 20 to 50 g; the bean-containing minestrone soup compositions are provided in a serving size from 20 to 50 g; the quinoa-containing minestrone soup compositions are provided in a serving size from 20 to 50 g; the pumpkin soup compositions are provided in a serving size from 20 to 50; the first vegetable both compositions are provided in a serving size from 5 to 15; the second vegetable both compositions are provided in a serving size from 3 to 15; and Energy Drink composition is provided in serving size of 1 to 5 oz.

The table set forth below provides a schedule of administration for two FMD meal plans to be administered to a subject. The Prolon Meal plan is useful for weight loss, treating or preventing hypertension, metabolic disease, diabetes, and the like. The Chemolieve meal plan is useful for alleviating the side effect of chemotherapy. Therefore, the diet packages set forth herein can include instruction providing the schedules and instructions for administering the FMD to treat various conditions as set forth in the methods below.

Table of Meal Schedules

| COMPONENTS (single servings) | MEAL PLAN - PROLON US | | | | | MEAL PLAN CHEMOLIEVE US | | | | |
|---|---|---|---|---|---|---|---|---|---|---|
| | DAY 1 | DAY 2 | DAY 3 | DAY 4 | DAY 5 | DAY 1 | DAY 2 | DAY 3 | DAY 4 | DAY 5 |
| nut-containing nutrition bar (L-Bar Nut based) | 2 | 1 | 1 | 1 | 1 | 1 | — | — | — | 1 |
| cocoa-containing nutrition bar (L-Bar ChocoCrisp) - .83 oz. | 1 | 1 | — | 1 | — | — | — | — | — | — |
| First olive-containing composition (Sea Salt) - 0.73 oz | 1 | 1 | — | 1 | — | — | — | — | — | — |
| Second olive-containing composition (Garlic) - 0.73 oz | — | 1 | — | 1 | — | — | — | — | — | — |
| kale cracker composition, (35 g) | 1 | — | 1 | — | 1 | 1 | 1 | — | — | — |
| vegetable soup composition | — | — | — | 1 | — | 1 | — | — | 1 | — |
| mushroom soup composition | — | 1 | — | — | — | — | 1 | — | — | — |
| tomato soup composition | 1 | — | 1 | — | 1 | 1 | — | — | — | 1 |
| quinoa-containing minestrone soup composition | — | 1 | — | 1 | — | — | — | — | — | — |
| bean-containing minestrone soup composition | 1 | — | 1 | — | 1 | — | — | — | — | — |
| pumpkin soup composition, | — | — | — | — | — | — | — | 1 | — | — |
| First vegetable broth composition | — | — | — | — | — | — | — | 1 | — | 1 |
| Second vegetable broth composition (chicken) | — | — | — | — | — | — | 1 | — | 1 | — |
| Energy Drink | — | 1 | 1 | 1 | 1 | 1 | 1 | — | — | — |
| Tea - Spearmint | 1 | 1 | 1 | 1 | 1 | 1 | 1 | 1 | 1 | 1 |
| Tea - Lemon Spearmint | 1 | 1 | 1 | 1 | 1 | 1 | 1 | 1 | 1 | 1 |
| Tea - Hibiscus | — | 2 | 2 | 2 | 2 | — | — | — | — | — |
| Algal oil | 1 | — | — | — | 2 | 2 | — | — | — | 1 |
| NR-1 | 2 | 1 | 1 | 1 | 1 | 2 | 1 | 1 | 1 | 1 |

While exemplary embodiments are described above, it is not intended that these embodiments describe all possible forms of the invention. Rather, the words used in the specification are words of description rather than limitation, and it is understood that various changes may be made without departing from the spirit and scope of the invention.

Additionally, the features of various implementing embodiments may be combined to form further embodiments of the invention.

REFERENCES

1. Cosmi, L., Liotta, F., Maggi, E., Romagnani, S. & Annunziato, F. Th17 and non-classic Th1 cells in chronic inflammatory disorders: two sides of the same coin. *International archives of allergy and immunology* 164, 171-177, doi:10.1159/000363502 (2014).

2. Dornmair, K., Goebels, N., Weltzien, H. U., Wekerle, H. & Hohlfeld, R. T-cell-mediated autoimmunity: novel techniques to characterize autoreactive T-cell receptors. *The American journal of pathology* 163, 1215-1226, doi: 10.1016/S0002-9440(10)63481-5 (2003).

3. Fasano, A. & Shea-Donohue, T. Mechanisms of disease: the role of intestinal barrier function in the pathogenesis of gastrointestinal autoimmune diseases. *Nature clinical practice. Gastroenterology & hepatology* 2, 416-422, doi: 10.1038/ncpgasthep0259 (2005).

4. Eksioglu-Demiralp, E. et al. Phenotypic characteristics of B cells in Behcet's disease: increased activity in B cell subsets. *The Journal of rheumatology* 26, 826-832 (1999).

5. Holmen, N., Isaksson, S., Simren, M., Sjovall, H. & Ohman, L. CD4+CD25+regulatory T cells in irritable bowel syndrome patients. *Neurogastroenterology and motility: the official journal of the European Gastrointestinal Motility Society* 19, 119-125, doi:10.1111/j.1365-2982.2006.00878.x (2007).

6. Xavier, R. J. & Podolsky, D. K. Unravelling the pathogenesis of inflammatory bowel disease. *Nature* 448, 427-434, doi:10.1038/nature06005 (2007).

7. Rovedatti, L. et al. Differential regulation of interleukin 17 and interferon gamma production in inflammatory bowel disease. *Gut* 58, 1629-1636, doi:10.1136/gut.2009.182170 (2009).

8. Ueno, A. et al. Increased prevalence of circulating novel IL-17 secreting Foxp3 expressing CD4+T cells and defective suppressive function of circulating Foxp3+ regulatory cells support plasticity between Th17 and regulatory T cells in inflammatory bowel disease patients. *Inflammatory bowel diseases* 19, 2522-2534, doi:10.1097/MIB.0b013e3182a85709 (2013).

9. Jin, D. et al. Manipulation of Microbiome, a Promising Therapy for Inflammatory Bowel Diseases. *Journal of Clinical & Cellular Immunology* 05(04). doi:10.4172/2155-9899.1000234 (2014).

10. Mcilroy, J., Ianiro, G., Mukhopadhya, I., Hansen, R., & Hold, G. L. Review article: the gut microbiome in inflammatory bowel disease-avenues for microbial management. *Alimentary Pharmacology & Therapeutics* 47(1), 26-42. doi:10.1111/apt.14384 (2017).

11. Yang, J-Y., Lee, Y-S., Kim, Y., Lee, S-H., Ryu, S. et al. (2017). Gut commensal *Bacteroides acidifaciens* prevents obesity and improves insulin sensitivity in mice. Mucosal immunology, 10, 104-116. 12. O'Neill, I., Schofield, Z., & Hall, L. (2017). Exploring the role of the microbiota member *Bifidobacterium* in modulating immune-linked diseases. Emerging topics in life sciences, 1(4), 333-349. 13. Dupaul-Chicoine, J., Yeretssian, G., Doiron, K., Bergstrom, K. S., McIntire, C. R., LeBlanc, P. M., Meunier, C., Turbide, C., Gros, P., Beauchemin, N., et al. (2010). Control of intestinal homeostasis, colitis, and colitis-associated colorectal cancer by the inflammatory caspases. Immunity 32, 367-378.

14. Koblansky, A. A., Truax, A. D., Liu, R., Montgomery, S. A., Ding, S., Wilson, J. E., Brickey, W. J., M€uhlbauer, M., McFadden, R. M., Hu, P., et al. (2016). The innate immune receptor NLRX1 functions as a tumor suppressor by reducing colon tumorigenesis and key tumor-promoting signals. Cell Rep. 14, 2562-2575.

PUBLICATIONS

1. TITLE Manuscript Number: THELANCETNEUROLOGY-D-16-00304

2. Choi I Y, Piccio L, Childress P, Bollman B, Ghosh A, Brandhorst S, Suarez J, Michalsen A, Cross A H, Morgan T E, Wei M, Paul F, Bock M, Longo V D. A Diet Mimicking Fasting Promotes Regeneration and Reduces Autoimmunity and Multiple Sclerosis Symptoms. Cell reports. 2016; 15(10):2136-46. doi: 10.1016/j.celrep.2016.05.009. PubMed PMID: 27239035; PMCID: PMC4899145.

3. Brandhorst S, Choi I Y, Wei M, Cheng C W, Sedrakyan S, Navarrete G, Dubeau L, Yap LP, Park R, Vinciguerra M, Di Biase S, Mirzaei H, Mirisola M G, Childress P, Ji L, Groshen S, Penna F, Odetti P, Perin L, Conti P S, Ikeno Y, Kennedy B K, Cohen P, Morgan T E, Dorff T B, Longo V D. A Periodic Diet that Mimics Fasting Promotes Multi-System Regeneration, Enhanced Cognitive Performance, and Healthspan. Cell Metab. 2015; 22(1):86-99. doi: 10.1016/j.cmet.2015.05.012. PubMed PMID: 26094889; PMCID: PMC4509734.

4. Levine M E, Suarez J A, Brandhorst S, Balasubramanian P, Cheng C W, Madia F, Fontana L, Mirisola M G, Guevara-Aguirre J, Wan J, Passarino G, Kennedy B K, Wei M, Cohen P, Crimmins E M, Longo V D. Low protein intake is associated with a major reduction in IGF-1, cancer, and overall mortality in the 65 and younger but not older population. Cell Metab. 2014; 19(3):407-17. doi: 10.1016/j.cmet.2014.02.006. PubMed PMID: 24606898; PMCID: PMC3988204.

5. Longo V D, Mattson M P. Fasting: molecular mechanisms and clinical applications. Cell Metab. 2014; 19(2): 181-92. doi: 10.1016/j.cmet.2013.12.008. PubMed PMID: 24440038; PMCID: 3946160.

6. Wei M, Brandhorst S, Shelehchi M, Mirzaei H, Cheng C W, Budniak J, Groshen S, Mack W J, Guen E, Di Biase S, Cohen P, Morgan T E, Dorff T, Hong K, Michalsen A, Laviano A, Longo V D. Fasting-mimicking diet and markers/risk factors for aging, diabetes, cancer, and cardiovascular disease. Sci Transl Med. 2017; 9(377). PubMed PMID: 28202779.

What is claimed is:

1. A probiotic composition for gastrointestinal autoimmune and/or inflammatory disease, the probiotic composition comprising:
   a bacterial component that is a combination of *Bacteroides acidifaciens* and *Bifidobacterium choerinum* such that the *Bifidobacterium choerinum* enhances probiotic activity of *Bacteroides acidifaciens* to be administered for prevention and treatment of gastrointestinal autoimmune and/or inflammatory disease; and
   a protective component that stabilizes the bacterial component.

2. The probiotic composition of claim 1 wherein the bacterial component further comprises gut microbiota strains isolated from genera selected from the group consisting of *Lactobacillus*, *Allobaculum*, *Bifidobacterium*, and combinations thereof.

3. The probiotic composition of claim 2 wherein each bacterial component is present in an amount from about $10^3$ to about $10^{14}$ CFU/g of each bacterial component.

4. The probiotic composition of claim 1 wherein the protective component is selected from the group consisting of protective carriers, protective coating, and protective encapsulants.

5. The probiotic composition of claim 1 wherein the protective component is a liquid.

6. The probiotic composition of claim 5 wherein the liquid is a hydroxylated hydrocarbon carrier.

7. The probiotic composition of claim 5 wherein the liquid is a polyol.

8. The probiotic composition of claim 1 wherein the protective component includes a stabilization agent that interacts with or encapsulates the bacterial component.

9. The probiotic composition of claim 8 wherein the stabilization agent is selected from the group consisting of adonitol, betaine, carbohydrates, proteins, amino acids, mixtures of sugar and protein, gums and skim milk, and combinations thereof.

10. The probiotic composition of claim 9 wherein the stabilization agent is dissolved or dispersed in a liquid.

11. The probiotic composition of claim 1 wherein the protective component encapsulates the bacterial component.

12. The probiotic composition of claim 11 wherein the bacterial component is encapsulated by spray drying, fluidized bed drying, or vacuum drying.

13. The probiotic composition of claim 11 wherein the protective component includes an encapsulating agent selected from the group consisting of maltodextrins, skim milk, reconstituted skim milk, casein, soybean protein, trehalose, and combinations thereof.

14. The probiotic composition of claim 1 further comprising an additive selected from the group consisting of any suitable adjuvants, excipients, additives, additional therapeutic agents, bioavailability enhancers, side-effect suppressing components, diluents, buffers, flavoring agents, binders, preservatives or other ingredients and combinations thereof.

15. The probiotic composition of claim 1 incorporated into a capsule.

* * * * *

UNITED STATES PATENT AND TRADEMARK OFFICE
CERTIFICATE OF CORRECTION

| | | Page 1 of 1 |
|---|---|---|
| PATENT NO. | : 11,504,408 B2 | |
| APPLICATION NO. | : 16/976952 | |
| DATED | : November 22, 2022 | |
| INVENTOR(S) | : Valter D. Longo et al. | |

It is certified that error appears in the above-identified patent and that said Letters Patent is hereby corrected as shown below:

In the Specification

Column 1, Line 16, insert:
--STATEMENT REGARDING FEDERALLY SPONSORED RESEARCH OR DEVELOPMENT
This invention was made with government support under Grant Nos. AG020642, AG025135, AG055369, and AG034906, awarded by the National Institutes of Health. The government has certain rights in the invention.--

Signed and Sealed this
Eighteenth Day of April, 2023

Katherine Kelly Vidal
*Director of the United States Patent and Trademark Office*